United States Patent
Goodman et al.

(10) Patent No.: US 11,246,495 B2
(45) Date of Patent: Feb. 15, 2022

(54) SYSTEM AND METHOD FOR MONITORING AORTIC PULSE WAVE VELOCITY AND BLOOD PRESSURE

(71) Applicant: Vital Sines International Inc., Mississauga (CA)

(72) Inventors: Jesse Goodman, Mississauga (CA); Benoit Lewden, Calgary (CA)

(73) Assignee: Vital Sines International Inc., Mississauga (CA)

(*) Notice: Subject to any disclaimer, the term of this patent is extended or adjusted under 35 U.S.C. 154(b) by 907 days.

(21) Appl. No.: 15/522,091

(22) PCT Filed: Oct. 27, 2015

(86) PCT No.: PCT/CA2015/051093
§ 371 (c)(1),
(2) Date: Apr. 26, 2017

(87) PCT Pub. No.: WO2016/065469
PCT Pub. Date: May 6, 2016

(65) Prior Publication Data
US 2018/0256044 A1    Sep. 13, 2018

Related U.S. Application Data

(60) Provisional application No. 62/069,106, filed on Oct. 27, 2014.

(51) Int. Cl.
*A61B 5/021* (2006.01)
*A61B 5/00* (2006.01)
(Continued)

(52) U.S. Cl.
CPC .......... *A61B 5/02125* (2013.01); *A61B 5/024* (2013.01); *A61B 5/7239* (2013.01);
(Continued)

(58) Field of Classification Search
None
See application file for complete search history.

(56) References Cited

U.S. PATENT DOCUMENTS 2,658,505 A    11/1953    Sheer
2,875,750 A    3/1959    Boucke et al.
(Continued)

FOREIGN PATENT DOCUMENTS

CA    2965710 A1    5/2016
CN    102197996 A    9/2011
(Continued)

OTHER PUBLICATIONS

Xia, Jingjing, and Simon Liao. "Cardiovascular Diseases Detecting via Pulse Analysis." Engineering 5.10 (2013): 176-180. (Year: 2013).*
(Continued)

*Primary Examiner* — Jacqueline Cheng
*Assistant Examiner* — Jairo H Portillo
(74) *Attorney, Agent, or Firm* — Bereskin & Parr LLP/S.E.N.C.R.L., s.r.l.; Tony Orsi; T. Cameron Gale

(57) ABSTRACT

Various embodiments are described herein for a system and a method for monitoring aortic pulse wave velocity and blood pressure. A pulse sensor is located on the exterior of an individual's body at a sensor location that allows acquisition of the pulse signal such that a reflected wave component of the pulse signal is present and allows characterization of reflected wave onset. A pulse signal is received from the pulse sensor and a reflected wave onset point is identified in the pulse signal. A reflected wave ratio is determined at the reflected wave onset point and the aortic pulse wave velocity is determined from the reflected wave ratio. The aortic pulse wave velocity can be displayed to the individual, transmitted to an external device and/or stored.

28 Claims, 11 Drawing Sheets

(51) Int. Cl.
*A61B 5/024* (2006.01)
*A61B 5/02* (2006.01)
*A61B 5/0285* (2006.01)

(52) U.S. Cl.
CPC ......... *A61B 5/02007* (2013.01); *A61B 5/0285* (2013.01); *A61B 5/02116* (2013.01)

(56) References Cited

U.S. PATENT DOCUMENTS

| | | |
|---|---|---|
| 2,944,542 A | 7/1960 | Barnett et al. |
| 3,090,377 A | 5/1963 | Salisbury et al. |
| 3,132,643 A | 5/1964 | Baum et al. |
| 3,648,686 A | 3/1972 | Payne |
| 3,998,550 A | 12/1976 | Konishi et al. |
| 4,355,642 A | 10/1982 | Alferness |
| 4,418,700 A | 12/1983 | Warner |
| 4,432,374 A | 2/1984 | Osanai |
| 4,510,941 A | 4/1985 | Semrow et al. |
| 4,685,464 A | 8/1987 | Goldberger et al. |
| 4,807,638 A | 2/1989 | Sramek |
| 4,869,261 A | 9/1989 | Penáz |
| 4,896,262 A | 1/1990 | Wayama et al. |
| 4,927,264 A | 5/1990 | Shiga et al. |
| 4,928,014 A | 5/1990 | Rosenthal |
| 4,938,218 A | 7/1990 | Goodman et al. |
| 5,002,061 A | 3/1991 | Close et al. |
| 5,111,817 A | 5/1992 | Clark et al. |
| 5,140,990 A | 8/1992 | Jones et al. |
| 5,146,926 A | 9/1992 | Cohen |
| 5,152,296 A | 10/1992 | Simons |
| 5,237,997 A | 8/1993 | Greubel et al. |
| 5,265,011 A | 11/1993 | O'Rourke |
| 5,269,310 A | 12/1993 | Jones et al. |
| 5,273,036 A | 12/1993 | Kronberg et al. |
| 5,293,874 A | 3/1994 | Takahashi et al. |
| 5,309,916 A * | 5/1994 | Hatschek ............ A61B 5/021 600/485 |
| 5,351,695 A | 10/1994 | Mills et al. |
| 5,396,893 A | 3/1995 | Oberg et al. |
| 5,423,322 A | 6/1995 | Clark et al. |
| 5,485,848 A | 1/1996 | Jackson et al. |
| 5,497,778 A | 3/1996 | Hon |
| 5,511,546 A | 4/1996 | Hon |
| 5,546,943 A | 8/1996 | Gould |
| 5,560,366 A | 10/1996 | Harada et al. |
| 5,626,140 A | 5/1997 | Feldman et al. |
| 5,649,543 A | 7/1997 | Hosaka et al. |
| 5,685,299 A | 11/1997 | Diab et al. |
| 5,704,363 A | 1/1998 | Amano |
| 5,713,350 A | 2/1998 | Yokota et al. |
| 5,715,826 A | 2/1998 | Horrocks et al. |
| 5,720,619 A | 2/1998 | Fisslinger |
| 5,734,373 A | 3/1998 | Rosenberg et al. |
| 5,741,217 A | 4/1998 | Gero |
| 5,766,132 A | 6/1998 | Yasukawa et al. |
| 5,784,151 A | 7/1998 | Miller et al. |
| 5,800,349 A | 9/1998 | Isaacson et al. |
| 5,827,179 A | 10/1998 | Lichter et al. |
| 5,853,364 A | 12/1998 | Baker, Jr. et al. |
| 5,862,805 A | 1/1999 | Nitzan |
| 5,865,755 A | 2/1999 | Golub |
| 5,876,348 A | 3/1999 | Sugo et al. |
| 5,882,311 A | 3/1999 | O'Rourke |
| 5,941,837 A | 8/1999 | Amano et al. |
| 5,961,467 A | 10/1999 | Shimazu et al. |
| 5,964,701 A | 10/1999 | Asada et al. |
| 5,974,124 A | 10/1999 | Schlueter, Jr. et al. |
| 5,987,519 A | 11/1999 | Peifer et al. |
| 5,990,866 A | 11/1999 | Yollin |
| 6,015,384 A * | 1/2000 | Ramamurthy .......... A61B 8/06 600/440 |
| 6,017,313 A | 1/2000 | Bratteli et al. |
| 6,038,666 A | 3/2000 | Hsu et al. |
| 6,047,203 A | 4/2000 | Sackner et al. |
| 6,093,146 A | 7/2000 | Filangeri |
| 6,095,985 A | 8/2000 | Raymond et al. |
| 6,144,552 A | 11/2000 | Whitcher et al. |
| 6,163,715 A | 12/2000 | Larsen et al. |
| 6,168,563 B1 | 1/2001 | Brown |
| 6,190,314 B1 | 2/2001 | Ark et al. |
| 6,222,189 B1 | 4/2001 | Misner et al. |
| 6,264,614 B1 | 7/2001 | Albert et al. |
| 6,266,546 B1 | 7/2001 | Steuer et al. |
| 6,290,650 B1 | 9/2001 | Butterfield et al. |
| 6,302,844 B1 | 10/2001 | Walker et al. |
| 6,317,834 B1 | 11/2001 | Gennaro et al. |
| 6,331,162 B1 | 12/2001 | Mitchell |
| 6,336,900 B1 | 1/2002 | Alleckson et al. |
| 6,371,921 B1 | 4/2002 | Caro et al. |
| 6,401,097 B1 | 6/2002 | McCotter et al. |
| 6,416,471 B1 | 7/2002 | Kumar et al. |
| 6,496,711 B1 | 12/2002 | Athan et al. |
| 6,558,320 B1 | 5/2003 | Causey, III et al. |
| 6,616,613 B1 | 9/2003 | Goodman |
| 8,273,030 B2 | 9/2012 | Harpas et al. |
| 2002/0072681 A1 | 6/2002 | Schnali |
| 2003/0004420 A1 | 1/2003 | Narimatsu |
| 2003/0036685 A1 | 2/2003 | Goodman |
| 2003/0167014 A1* | 9/2003 | Ogura ................. A61B 5/02007 600/513 |
| 2003/0199775 A1* | 10/2003 | Narimatsu .......... A61B 5/02007 600/490 |
| 2004/0171947 A1* | 9/2004 | Ogura ...................... A61B 5/02 600/500 |
| 2009/0030328 A1 | 1/2009 | Harpas et al. |
| 2009/0076398 A1 | 3/2009 | Li et al. |
| 2010/0292589 A1 | 11/2010 | Goodman |
| 2012/0197088 A1* | 8/2012 | Karamanoglu .... A61B 5/02116 600/300 |
| 2013/0079606 A1 | 3/2013 | McGonigle et al. |
| 2013/0184596 A1* | 7/2013 | Fujii ................. A61B 5/02125 600/492 |
| 2015/0133806 A1* | 5/2015 | Airaksinen .......... A61B 5/7246 600/513 |

FOREIGN PATENT DOCUMENTS

| | | |
|---|---|---|
| CN | 103054562 A | 4/2013 |
| EP | 0443267 A1 | 8/1991 |
| EP | 2554111 A1 | 6/2013 |
| EP | 3212070 A1 | 9/2017 |
| GB | 2356250 A | 5/2001 |
| GB | 2356251 A | 5/2001 |
| GB | 2356252 A | 5/2001 |
| JP | H07-39530 A | 2/1995 |
| JP | H10-254985 A | 9/1998 |
| JP | H11-85891 A | 3/1999 |
| JP | 2004-195204 A | 7/2004 |
| JP | 2012-85792 A | 5/2012 |
| WO | 98/59487 A1 | 12/1998 |
| WO | 99/32030 A1 | 7/1999 |
| WO | 99/60755 A1 | 11/1999 |
| WO | 2016065469 A1 | 5/2016 |

OTHER PUBLICATIONS

Karamanoglu, Mustafa. "A system for analysis of arterial blood pressure waveforms in humans." Computers and biomedical research 30.3 (1997): 244-255. (Year: 1997).*

Josep Maria Solà I Carós M. Sc. Telecommunications, Universitat Politècnica de Catalunya, Diss. ETH. No. 20093, Continuous non-invasive blood pressure estimation, A dissertation submitted to ETH Zurich for the Degree of Doctor of Sciences, accepted 2011.

Yan Chen et al., Continuous and Noninvasive Measurement of Systolic and Diastolic Blood Pressure by One Mathematical Model with the Same Model Parameters and Two Separate Pulse Wave Velocities, Annals of Biomedical Engineering, vol. 40, No. 4, Apr. 2012, pp. 871-882.

G. Fortino and V. Giampà, "PPG-based methods for non invasive and continuous blood pressure measurement: an overview and

(56) References Cited

OTHER PUBLICATIONS development issues in body sensor networks," 2010 IEEE International Workshop on Medical Measurements and Applications, Ottawa, ON, 2010, pp. 10-13.
Kozo Hirata et al. Pulse Wave Analysis and Pulse Wave Velocity—A Review of Blood Pressure Interpretation 100 Years After Korotkov—Circulation Journal, vol. 70, Oct. 2006, pp. 1231-1239.
Zbignevs Marcinkevics et al., Relationship between arterial pressure and pulse wave velocity using photoplethysmography during the post-exercise recovery period, Acta Universitatis Latviensis, 2009, vol. 753, Biology, pp. 59-68.
Sandrine C. Millasseau et al., Noninvasive Assessment of the Digital Volume Pulse Comparison With the Peripheral Pressure Pulse, Hypertension 2000; 36; 952-956.
S. C. Millasseau et al., Determination of age-related increases in large artery stiffness by digital pulse contour analysis, Clinical Science (2002) 103, 371-377 (Printed in Great Britain).
Jan Muller et al., Oscillometric Carotid to Femoral Pulse Wave Velocity Estimated With the Vicorder Device, The Journal of Clinical Hypertension vol. 15 | No. 3 | Mar. 2013, pp. 176-179.
Juan M. Padilla et al. Pulse Wave Velocity and Digital Volume Pulse as Indirect Estimators of Blood Pressure: Pilot Study on Healthy Volunteers, Cardiovasc Eng, Springer Science + Business Media, LLC; published online: Aug. 6, 2009.
Gary L. Pierce et al., Aortic pulse wave velocity and reflecting distance estimation from peripheral waveforms in humans: detection of age- and exercise training-related differences, Am J Physiol Heart Circ Physiol 305: H135-H142, 2013.
K. Pilt et al., Possibility to Use Finapres Signal for the Estimation of Aortic Pulse Wave Velocity, A. Jobbagy (Ed.), 5th European IFMBE Conference, IFMBE Proceedings 37, pp. 524-527, 2011.
Sorvoja, Hannu, Noninvasive blood pressure pulse detection and blood pressure determination, Faculty of Technology, University of Oulu, P.O.Box 4000, FI-90014 University of Oulu, Finland, Department of Electrical and Information Engineering, Infotech Oulu, University of Oulu, P.O.Box 4500, FI-90014 University of Oulu, Finland Acta Univ. Oul. C 259, 2006 Oulu, Finland.
Isabella Tan et al., Heart Rate Dependence of Aortic Pulse Wave Velocity at Different Arterial Pressures in Rats, Hypertension, 2012; 60: pp. 528-533.
Michael Theodor et al., Implantable Acceleration Plethysmography for Blood Pressure Determination, 35th Annual International Conference of the IEEE EMBS, Osaka, Japan, Jul. 3-7, 2013, pp. 4038-4041.
Determinants of pulse wave velocity in healthy people and in the presence of cardiovascular risk factors: 'establishing normal and reference values' The Reference Values for Arterial Stiffness' Collaboration, European Heart Journal, vol. 31, Issue 19, Oct. 1, 2010, pp. 2338-2350 http://eurheartj.oxfordjournals.org/content/31/19/2338.
International Search Report/Written Opinion (ISRWO) for corresponding international application PCT/CA2015/051093, dated Feb. 8, 2016.
Jess Goodman, Oximeter signaling: There's more than meets the eye—Analog Wire—Blogs—T1 E2E Community printed Sep. 4, 2014.
Asmar R. et al. Assessment of arterial distensibility by automatic pulse wave velocity measurement. Validation and clinical studies. Hypertension. Sep. 1995; 26(3): 485-90.
Extended European Search Report (EESR) for corresponding European patent publication EP 3212070, dated Apr. 24, 2018.
Chapter 30: Arterial Pressure Waveforms http://web.squ.edu.om/med-Lib/MED_CD/E_CDs/anesthesia/site/co . . . printed Jul. 24, 2014.
Ammar W. Ashor, Jose Lara, Mario Siervo, Carlos Celis-Morales, John C. Mathers. Effects of Exercise Modalities on Arterial Stiffness and Wave Reflection: A Systematic Review and Meta-Analysis of Randomized Controlled Trials. Published: Oct. 15, 2014, https://doi.org/10.1371/journal.pone.0110034.

Office Action and Search Report dated Jul. 22, 2019 in corresponding CN Patent Application No. 201580058802.0.
Notice of Reasons for Refusal and Search Report dated Jul. 30, 2019 in corresponding JP Patent Application No. 2017-523917.
O'Rourke et al., "Wave Reflection in the Systemic Circulation and its Implications in Ventricular Function", Journal of Hypertension, 1993,11(4): 327-337.
Liu et al., "Aortic Compliance in Human Hypertension", Hypertension, 1989,14(2): 129-136.
Pruett, "Measurement of Pulse-Wave Velocity Using a Beat-Sampling Technique", Annals of Biomedical Engineering, 1988, 16(4): 341-347.
Rangayyan, Chapter 4, pp. 128-136, in "A Case-Study Approach to Solve Problems in Biomedical Signal Analysis", Wiley-IEEE Press, New Jersey: 2000.
Karamanoglu et al., "On-line Synthesis of the Human Ascending Aortic Pressure Pulse From the Finger Pulse", Hypertension, 1997, 30(6): 1416-1424.
Karamanoglu et al., "Functional Origin of Reflected Pressure Waves in a Multibranched Model of the Human Arterial System", Am J Physiol., 1994, 267(5 Pt 2): H1681-H1688.
Bulpitt et al., "Vascular Compliance as a Measure of Biological Age", JAGS, 1999, 47(6): 657-663.
Hopkins et al., A Family History of NIDDM Is Associated with Decreased Aortic Distensibility in Normal Healthy Young Adult Subjects, Diabetes Care, 1996, 19(5): 501-503.
Wright et al., "A micropocessor based photoplethysmograph for use in clinical practice", Anaesthesia, 1995, 50(10): 875-878.
Stitt, "AC Coupling Instrumentation and Difference Amplifiers", Application Bulletin 1991.
Pallás-Areny et al., "AC Instrumentation Amplifier for Bioimpedance Measurements", IEEE Transactions on Biomedical Engineering, 1993, 40(8): 830-833.
McVeigh, "Age-Related Abnormalities in Arterial Compliance Identified by Pressure Pulse Contour Analysis", Hypertension, 1999, 33(6): 1392-1398.
Lichstein et al., "An Integrated Blood Volume Pulse Biofeedback System for Migraine Treatment", Biofeed-back and Self-Regulation, 1983, 8(1): 127-134.
Lu et al., "An Ultra-High Common-Mode Rejection Ratio (CMRR) AC Instrumentation Amplifier for Laplacian Electrocardiographic Measurement", Instrumentation Research, 1999, 33(1): 76-83.
Lehmann et al., "Aortic Distensibility in Patients with Cerebrovascular Disease", Clinical Science, 1995, 89(3): 247-253.
Kingwell et al., "Arterial compliance increases after moderate-intensity cycling", American Journal of Physiology, 1997, 273(5): 2186-2191.
Hayes et al., "Artifact reduction in photoplethysmography", Applied Optics, 1998, 37(31): 7437-7446.
Takazawa et al., "Assessment of Vasoactive Agents and Vascular Aging by the Second Derivative of Photoplethysmogram Waveform", Hypertension, 1998, 32(2): 365-370.
Bernardi et al., "Autonomic control of Skin microVessels: assessment by power Spectrum of photoplethysmographic waves", Clinical Science, 1996, 90(5): 345-355.
Steptoe, "Blood Pressure Control: A Comparison of Feedback and Instructions Using Pulse Wave Velocity Measurements", Psychophysiology, 1976, 13(6): 528-535.
London et al., "Body height as a determinant of carotid pulse contour in humans", Hypertension, 1992, 10(6): S93-S95.
Benthin et al., "Calculation of Pulse-Wave Velocity. Using Cross Correlation-Effects of Reflexes in the Arterial Tree", Ultrasound in Medicine & Biology, 1991, 17(5): 461-469.
Walsh et al., "Comparison of Biofeedback Pulse Wave Velocity and Progressive Relaxation in Essential Hypertensives", Perceptual and Motor Skills, 1977, 44: 839-843.
Lapointe et al., "Computation of Aortic Pulse Wave Velocity and Aortic Extensibility from Pressure Gradient Measurements", Canadian Journal of Physiology Pharmacology, 1975, 53(5): 940-946.
Hayano et al., "Continuous assessment of hemodynamic control by complex demodulation of cardiovascular variability", American Journal of Physiology, 1993, 264(4 Pt 2): H1229-1238.

(56) References Cited

OTHER PUBLICATIONS

Berger et al., "Differential effects of wave reflections a peripheral resistance on aortic blood pressure: a model-based study", American Journal of Physiology, 1994, 266(4 Pt 2): H1626-1642.
Laederach-Hofmann et al., "Early autonomic dysfunction in patients with diabetes mellitus assessed by spectral analysis of heart rate and blood pressure variability", Clinical Physiology, 19(2): 97-106.
Belz, "Elastic Properties and Windkessel Function of the Human Aorta", Cardiovasc. Drugs Ther., 1995, 9(1): 73-83.
Chen et al., "Estimation of Central Aortic Pressure Waveform by Mathematical Transformation of Radial Tonometry Pressure", Circulation, 1997, 95(7): 1827-1836.
Chang et al., "Exponentially Tapered T-tube Model in the Characterization of Arterial Non-uniformity", J. Theor. Biology, 1996, 183(1): 35-46.
Lieberman, "Fundamentals of clinical cardiology", American Heart Journal, 1980, 99(4): 517-527.
Westerhof et al., "Haemodynamic basis for the development of left ventricular failure in systolic hypertension and for its logical therapy", Journal of Hypertension, 1995, 13(9): 943-952.
Abel, "Influence of Aortic Compliance on Coronary Blood Flow", Circulatory Shock, 1984, 12(4): 265-276.
"Lifeshirt.com, Vital Signs Online", screen capture of web page Mar. 2, 2000 <https://web.archive.org/web/20000302203039/http://www.lifeshirt.com/pubdocs/overview.html> (1 page).
Murgo et al., "Manipulation of Ascending Aortic Pressure and Flow Wave Reflections with the Valsalva Maneuver: Relationship to Input Impedance", Circulation, 1981, 63(1): 122-132.
Huikuri et al., "Measurement of Heart Rate Variability: A Clinical Tool or a Research Toy?", Journal of the American College of Cardiology, 1999, 34(7): 1878-1883.
Nakajima et al., "Monitoring of heart and respiratory rates by photoplethysmography using a digital filtering technique", Med. Eng. Phys., 1996, 18(5): 365-372.
Lindberg et al., "Monitoring of respiratory and heart rates using a fibre-optic sensor", Medical & Biological Engineering & Computing, 1992, 30(5): 533-537.
Latham et al., "Nonhuman primate model for regional wave travel and reflections along aortas", American Journal of Physiology, 1987, 253(2 Pt 2): H299-306.
Kelly et al., "Noninvasive Determination of Age-Related Changes in the Human Arterial Pulse", Circulation, 1989, 80(6): 1652-1659.
Liang et al., "Non-invasive measurements of arterial Structure and function: repeatability interrelationships and trial Sample size", Clinical Science, 1998, 95(6): 669-679.
Mendelson et al., "Noninvasive Pulse Oximetry Utilizing Skin Reflectance Photoplethysmography", IEEE Transactions of Biomedical Engineering, 1988, 35(10): 798-805.
Dorlas et al., "Photo-Electric Plethysmography as a Monitoring Device in Anaesthesia", British Journal of Anaesthesiology, 1985, 57(5): 524-530.
Chowienczyk et al., "Photoplethysmographic Assessment of Pulse Wave Reflection" Journal of the American College of Cardiology, 1999, 34(7): 2007-2014.
Karamanoglu et al., "Pressure wave propagation in a multibranched model of the human upper limb", American Journal of Physiology, 1995, 269(4 Pt 2): H1363-1369.
O'Rourke et al., "Pulsatile Flow and Pressure in Human Systemic Arteries", Circulation Research, 1980, 46(3): 363-372.
O'Rourke, "Pulse wave analysis", J Hypertens Suppl., 1996, 14(5): S147-157.
Wilkinson et al., "Pulse Wave Analysis and Arterial Stiffness", Journal of Cardiovascular Pharmacology, 1998, 32 Suppl 3: S33-37.
Van Den Bos et al., "Reflection in the systemic arterial system: effects of aortic and carotid occlusion", Cardiovascular Research, 1976, 10(5): 565-573.
Latham et al., "Regional wave travel and reflections along the human aorta: a study with Six Simultaneous micromanometric pressures", Circulation, 1985, 72(6): 1257-1269.

Buby et al., "Relaxation pretraining, pulse wave velocity and thermal biofeedback in the treatment of essential hypertension", International Journal of Psychophysiology, 1990, 9(3): 225-230.
Okada et al., "Role of pulse wave Velocity for assessing autonomic nervous system activities in reference to heart rate variability", Medical Information, 1996, 21(1): 81-90.
Steptoe et al., "The Control of Blood Pressure Using Pulse-Wave Velocity Feedback", Journal of Psychosomatic Research, 1976, 20(5): 417-424.
Busse et al., "The Genesis of the Pulse Contours of the Distal Leg Arteries in Man", Pflügers Archiv., 1975, 360: 63-79.
Wang et al., "Time-Frequency Distribution Technique in Biological Signal Processing" Biomedical Instrumentation & Technology, 1995, 29(3): 203-212.
O'Rourke, "Towards Optimization of Wave Reflection: Therapeutic Goal for Tomorrow?", Clin. Exp. Pharmacol. Physiol., 1996, 23(Suppl. 1): S11-S15.
Burattini et al., "Two Arterial Effective Reflecting Sites May Appear as One to the Heart", Circulation Research, 1991, 68: 85-99.
Pitson et al., "Use of Pulse Transit Time as a Measure of Inspiratory Effort in Patients with Obstructive Sleep Apnoea", Eur. Respir. J., 1995, 8(10): 1669-1674.
Visram, "Use of Two Oximeters to Investigate a Method of Movement Artefact Rejection Using Photoplethysmographic Signals", British Journal of Anaesthesia, 1994, 72(4): 388-392.
Pitson et al., "Value to Beat-to-Beat Blood Pressure Changes, Detected By Pulse Transit Time, in the Management of the Obstructive Sleep Apnoea/Hypopnoea Syndrome", Eur., Respir. J., 1998, 12(3): 685-692.
O'Rourke et al., "Wave Reflections and the Arterial Pulse", Arch. Intern. Med., 1984, 144(2): 366-371.
Harland et al., "Electric potential probes-new directions in the remote sensing of the human body", Measurement Science and Technology, 2002, 13(2): 163-169.
Yang et al., "Sensor Fusion For Noninvasive Continuous Monitoring Of Pulsating Blood Pressure Based On An Arterial Hemodynamic Model", MIT, 2000, 8 pages.
"ProComp+ encoder and sensor instructions", Thought Technology Ltd., Tech Note 009, pp. 1-11, accessed on Jun. 24, 2002 <www.thoughttechnology.com/gsr.htm>.
"Electrical Impedance Mini-Lab—Impedance Plethysmograph System Model IPG-104", RJL Systems, Inc., 1986-2000 <http://www.rjlsystems.com/research/ipg1.html; www.rjlsystems.com/research/ipg_specs.html; www.rjlsystems.com/research/ipg_functions.html> (12 pages).
"Medis—Product Overview", Medizinische Messtechnik GmbH, Dec. 20, 2000 <http://www.medis-de.com/en/products.html; http://www.medis-de.com/en/light.html; http://www.medis-de.com/en/compact.html> (10 pages).
"Continuous Blood Pressure Device (CBPD)", NASA, Jun. 21, 2000 <https://web.archive.org/web/20010218010059/http://hrf.jSc.nasa.gov/cbpd.htm> (2 pages).
TNO Biomedical Instrumentation, screen capture of web page (Jun. 9, 2001) <https://web.archive.org/web/20010609041758/http://www.bmi-tno.nl/home_en.htm> (1 page).
Healey, "The PalmPilot Interface", Feb. 12, 1999 <http://vismod.www.media.mit.edu/tech-reports/TR-478/node3.html; http://vismod.www.media.mit.edu/tech-reports/TR-478/node1.html> (3 pages).
Hayes et al., "Quantitative Investigation of Artefact in Photoplethysmography and Pulse Oximetry for Respiratory Exercise Testing", accessed on Jun. 18, 1999 <http://www.lboro.ac.uk/departments/el/research/optics/ppgraphy/paper2c.htm> (5 pages).
Smith et al., "Detection, Suppression And Reduction Of Motion Artefact In Arterial Near Infrared Plethysmography", Presented at INABIS '98—5th Internet World Congress on Biomedical Sciences at McMaster University, Dec. 7-16, 1998, Hamilton, Ontario, Canada <http://www.mcmaster.ca/inabis98/cvdisease/smith0901/two.html> (4 pages).
Appleyard, "A Historical Perspective of Hemodynamics", accessed on May 1, 1999 <http://hemodynamics.ucdavis.edu/appleyard's%20review/history_Appleyard.htm> (10 pages).

* cited by examiner

SYSTEM AND METHOD FOR MONITORING AORTIC PULSE WAVE VELOCITY AND BLOOD PRESSURE

CROSS-REFERENCE TO RELATED APPLICATION

This application claims priority from U.S. provisional patent application No. 62/069,106, filed Oct. 27, 2014 entitled "SYSTEM AND METHOD FOR MONITORING AORTIC PULSE WAVE VELOCITY AND BLOOD PRESSURE", the disclosure of which is incorporated herein, in its entirety, by reference.

FIELD

The various embodiments described herein generally relate to a system and method for monitoring aortic pulse wave velocity and blood pressure, and in particular systems using a single external pulse sensor.

BACKGROUND

Pulse signals contain important information about the status of an individual's health. Arterial pulse signals contain three waves that interact to define the shape of the pulse signal. A primary wave is associated with cardiac contraction; a reflected wave is formed as a summation of primary wave reflections; and a dicrotic wave occurs when the Aortic Valve closes at the end of the cardiac contraction phase, or systole.

The primary, reflected and dicrotic waves can be identified in an arterial pulse signal acquired from most individuals. Typically, identification of these waveforms and their characteristics requires the use of time domain or frequency domain signal analysis methods. These waveforms can be used to determine an aortic pulse wave velocity (AoPWV) of the arterial pulse signal.

AoPWV has been correlated with changes in blood pressure over the short term and changes in aortic stiffness over the longer term. Aortic stiffness has been identified as an effective cardiac risk indicator and has also been shown to be a predictor of risk of death from all causes.

Currently, there are several methods for determining an individual's AoPWV. The 'gold standard' method to determine AoPWV involves the use of at least two arterial pulse sensors placed over the carotid and femoral arteries. Another method to determine AoPWV is to acquire the brachial arterial pressure pulse signal using an inflatable cuff applied to an arm. The acquired signals are often used with a calculated effective aortic reflecting distance and pulse signal analysis which are then used to determine AoPWV. Generally, known methods for acquiring pulse signals for AoPWV analysis require the use of sophisticated hardware or are invasive.

SUMMARY OF VARIOUS EMBODIMENTS

In a broad aspect, at least one embodiment described herein provides a method for monitoring aortic pulse wave velocity. The method can include receiving a pulse signal from a sensor on the exterior of an individual's body where the sensor is positioned at a sensor location that allows acquisition of the pulse signal such that a reflected wave component of the pulse signal is present and allows characterization of reflected wave onset. A reflected wave onset point can be identified in the pulse signal. A reflected wave ratio can be determined at the reflected wave onset point and the aortic pulse wave velocity can be determined from the reflected wave ratio. The method also includes at least one of displaying the aortic pulse wave velocity, transmitting the aortic pulse wave velocity, and storing the aortic pulse wave velocity.

In some embodiments, identifying the reflected wave onset point may include determining a third derivative from the pulse signal, identifying a second peak of the third derivative and identifying the reflected wave onset point using the second peak of the third derivative.

In some embodiments, identifying the reflected wave onset point may include determining a third derivative and a fourth derivative from the pulse signal, identifying an onset point test window from the fourth derivative, identifying a first window peak of the third derivative in the onset point test window, and identifying the reflected wave onset point using the first window peak of the third derivative.

In some embodiments, determining the reflected wave ratio may include determining a first derivative from the pulse signal, identifying a first derivative onset point corresponding to the reflected wave onset point in the third derivative, and determining the reflected wave ratio as a normalized height of the first derivative onset point.

In some embodiments, determining the normalized height of the first derivative onset point may include identifying a first peak in the first derivative, measuring a height of the first peak, normalizing the first derivative based on the height of the first peak, and measuring a height of the normalized first derivative at the first derivative onset point.

In some embodiments, the aortic pulse wave velocity may be determined using a look-up table of mappings from the reflected wave ratio to the aortic pulse wave velocity.

In some embodiments, the method may further include determining a heart rate from the pulse signal, and determining a normalized aortic pulse wave velocity using a normalization factor determined from the heart rate. In some embodiments, determining the normalized aortic pulse wave velocity may include determining a normalized reflected wave ratio using a normalization factor determined from the heart rate and then determining the normalized aortic pulse wave velocity using the normalized reflected wave ratio.

In some embodiments, the method may include calibrating blood pressure factors for the individual, and determining the individual's blood pressure using the aortic pulse wave velocity and the blood pressure factors In some embodiments, prior to identifying the reflected wave onset point, it may be determined if the pulse signal satisfies an error threshold condition. The acts of identifying the reflected wave onset point, calculating the reflected wave ratio, and determining the aortic pulse wave velocity may only be performed if the pulse signal satisfies the error threshold condition.

In some embodiments, determining whether the pulse signal satisfies the error threshold condition may include determining a fourth derivative from the pulse signal. A first peak, a second peak, and a third peak from the fourth derivative may be identified, and it can be determined if the first peak, second peak, and the third peak satisfy a plurality of peak error conditions. The pulse signal may satisfy the error threshold condition if the first peak, second peak, and the third peak satisfy the plurality of peak error conditions.

In some embodiments, the plurality of peak error conditions may include a first threshold and a second threshold. The first peak and the second peak may be compared to determine if the second peak satisfies the first threshold, and the second peak and the third peak may be compared to determine if the third peak satisfies the second threshold. The pulse signal may satisfy the error threshold condition if both the first threshold and the second threshold are satisfied.

In some embodiments, a height of the second peak may be at least 80% of a height of the first peak to satisfy the first threshold, and a height of the third peak may be at least 10% of the height of the second peak to satisfy the second threshold.

In some embodiments, the plurality of peak error conditions may include an amplitude threshold, a first timing threshold, and a second timing threshold. The first peak and the second peak may be compared to determine if the second peak satisfies the amplitude threshold. A first distance between the first peak and the second peak and a second distance between the second peak and a third peak can be determined. The first distance and second distance may be compared to determine if the first timing threshold is satisfied. A third distance between the first peak and the third peak can be determined to determine if the second timing threshold is satisfied. The pulse signal may satisfy the error threshold condition if each of the amplitude threshold, the first timing threshold and the second timing threshold is satisfied.

In some embodiments, a height of the second peak may be at least 80% of a height of the first peak to satisfy the amplitude threshold, the second distance may be less than three times the first distance to satisfy the first timing threshold, and the third distance may be not less than 0.2 seconds to satisfy the second timing threshold.

In another broad aspect, at least one embodiment described herein provides a computer readable medium including a plurality of instructions that are executable on a microprocessor of a device for adapting the device to implement a method for monitoring aortic pulse wave velocity. The method for monitoring aortic pulse wave velocity may be defined in accordance with the various embodiments described in accordance with the teachings herein.

In another broad aspect, at least one embodiment described herein provides a system for monitoring aortic pulse wave velocity. The system may include a pulse acquisition unit configured to acquire a pulse signal from the exterior of an individual's body and a pulse analysis unit having at least one of a display unit, a storage unit and a communication interface. The pulse acquisition unit may be adapted to be positioned at a sensor location that allows acquisition of the pulse signal such that a reflected wave component of the pulse signal is present and allows characterization of reflected wave onset, and the pulse acquisition unit may be configured to transmit the pulse signal to the pulse analysis unit. The pulse analysis unit may be configured to identify a reflected wave onset point in the pulse signal, determine a reflected wave ratio at the reflected wave onset point, and determine the aortic pulse wave velocity from the reflected wave ratio. The pulse analysis unit may further be configured to perform at least one of displaying the aortic pulse wave velocity using the display unit, transmitting the aortic pulse wave velocity using the communication interface or storing the aortic pulse wave velocity using the storage unit.

In some embodiments, the pulse analysis unit may be configured to identify the reflected wave onset point by determining a third derivative from the pulse signal, identifying a second peak of the third derivative, and identifying the reflected wave onset point using the second peak of the third derivative.

In some embodiments, the pulse analysis unit may be configured to identify the reflected wave onset point by determining a third derivative and a fourth derivative from the pulse signal, identifying an onset point test window from the fourth derivative, identifying a first window peak of the third derivative in the onset point test window, and identifying the reflected wave onset point using the first window peak of the third derivative.

In some embodiments, the pulse analysis unit may be configured to determine the reflected wave ratio by determining a first derivative from the pulse signal, identifying a first derivative onset point corresponding to the reflected wave onset point in the third derivative, and determining the reflected wave ratio as a normalized height of the first derivative onset point.

In some embodiments, the pulse analysis unit may be configured to determine the normalized height of the first derivative onset point by identifying a first peak in the first derivative, measuring an height of the first peak, normalizing the first derivative based on the height of the first peak, and measuring a height of the normalized first derivative at the first derivative onset point.

In some embodiments, the pulse analysis unit may be configured to determine the aortic pulse wave velocity by using a look-up table of mappings from the reflected wave ratio to the aortic pulse wave velocity.

In some embodiments, the pulse analysis unit may be configured to determine a heart rate from the pulse signal, and determine a normalized aortic pulse wave velocity using a normalization factor determined from the heart rate.

In some embodiments, the pulse analysis unit may be configured to calibrate blood pressure factors for an individual and determine the individual's blood pressure using the aortic pulse wave velocity and the blood pressure factors. The pulse analysis unit may be configured to perform at least one of displaying the individual's blood pressure using the display unit, transmitting the individual's blood pressure using the communication interface, and storing the individual's blood pressure in the storage unit.

In some embodiments, the pulse analysis unit may be configured to determine if the pulse signal satisfies an error threshold condition prior to identifying the reflected wave onset point. The pulse analysis unit may perform the steps of identifying the reflected wave onset point, determining the reflected wave ratio, and determining the aortic pulse wave velocity only if the pulse signal satisfies the error threshold condition.

In some embodiments, the pulse analysis unit may further be configured to determine a fourth derivative from the pulse signal. The pulse analysis unit may identify a first peak, a second peak, and a third peak from the fourth derivative. The pulse analysis unit may determine if the first peak, the second peak, and the third peak satisfy a plurality of peak error conditions, and determine that the pulse signal satisfies the error threshold condition if the first peak, the second peak, and the third peak satisfy the plurality of peak error conditions.

In some embodiments, the plurality of peak error conditions may include a first threshold and a second threshold. The pulse analysis unit may compare the first peak and the second peak to determine if the second peak satisfies the first threshold and compare the second peak and the third peak to determine if the third peak satisfies the second threshold. The pulse analysis unit may determine that the pulse signal satisfies the error threshold condition if both the first threshold and the second threshold are satisfied. In some cases, a height of the second peak may be at least 80% of a height of the first peak to satisfy the first threshold, and a height of the third peak may be at least 10% of the height of the second peak to satisfy the second threshold.

In some embodiments, the plurality of peak error conditions may include an amplitude threshold, a first timing threshold, and a second timing threshold. The pulse analysis unit may compare the first peak and the second peak to determine if the second peak satisfies the amplitude threshold. The pulse analysis unit may determine a first distance between the first peak and the second peak and a second distance between the second peak and a third peak and compare the first distance and second distance to determine if the first timing threshold is satisfied. The pulse analysis unit may determine a third distance between the first peak and the third peak to determine if the second timing threshold is satisfied. The pulse analysis unit can also determine that the pulse signal satisfies the error threshold condition if each of the amplitude threshold, the first timing threshold and the second timing threshold is satisfied.

In some embodiments, a height of the second peak may be at least 80% of a height of the first peak to satisfy the amplitude threshold, the second distance may be less than three times the first distance to satisfy the first timing threshold, and the third distance may be not less than 0.2 seconds to satisfy the second timing threshold.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described.

Figure 1:
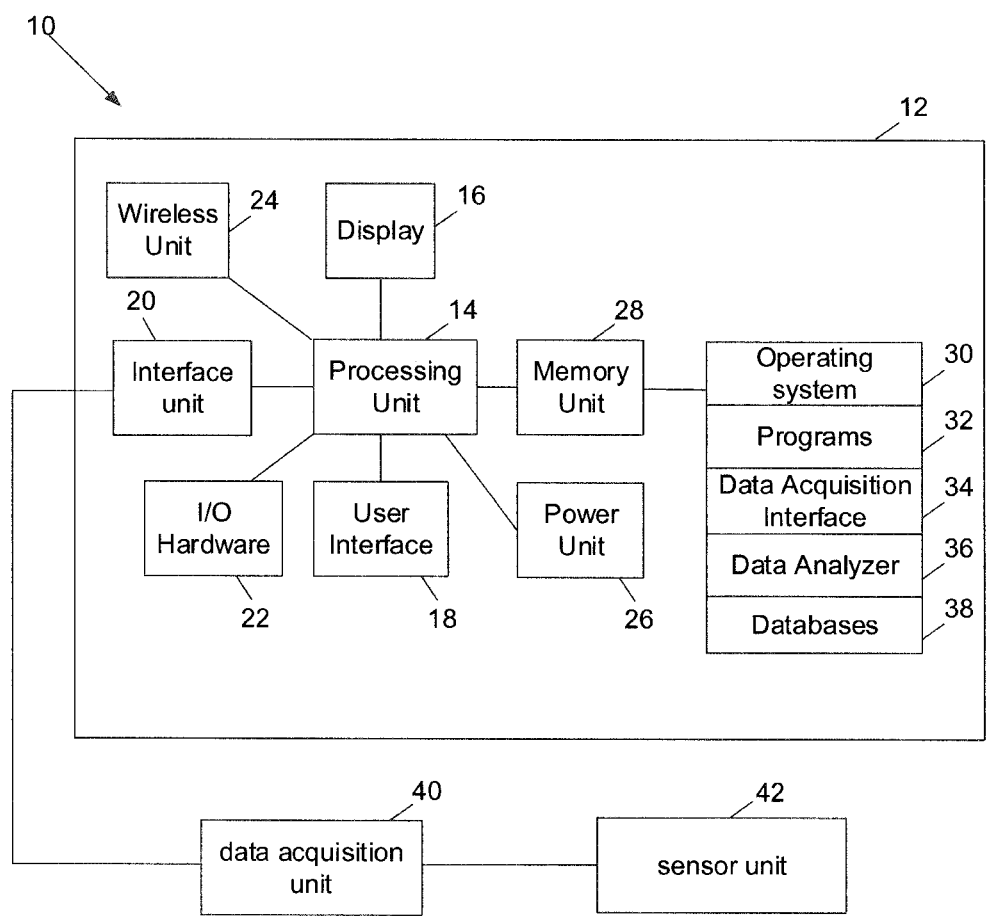
FIG. 1 is a block diagram of an example embodiment of a system for monitoring aortic pulse wave velocity and blood pressure.

Further aspects and features of the embodiments described herein will appear from the following description taken together with the accompanying drawings.

DETAILED DESCRIPTION OF THE EMBODIMENTS

Various systems or methods will be described below to provide an example of an embodiment of the claimed subject matter. No embodiment described below limits any claimed subject matter and any claimed subject matter may cover methods or systems that differ from those described below. The claimed subject matter is not limited to systems or methods having all of the features of any one system or method described below or to features common to multiple or all of the apparatuses or methods described below. It is possible that a system or method described below is not an embodiment that is recited in any claimed subject matter. Any subject matter disclosed in a system or method described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" may be used to indicate that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are various example embodiments of a system and method that may be used for monitoring aortic pulse wave velocity (AoPWV). Furthermore, at least some of the embodiments of the systems and methods described herein may also be used to monitor an individual's blood pressure using the aortic pulse wave velocity. In addition, at least some of the embodiments described herein may also be used to track changes in an individual's AoPWV and blood pressure over time as part of a health or fitness tracking program.

At least some of the embodiments described herein take into account that the effective aortic reflecting distance is a factor that increases with aging. Methods for determining effective aortic reflecting distance (and therefore AoPWV) typically introduce age, sex, weight and height as factors that will influence the calculated result.

At least one of the embodiments described herein, provides a system and/or method for determining AoPWV using an arterial pulse signal acquired in a simple, non-invasive and cost effective manner. At least one of the embodiments described herein, provides a system and/or method for obtaining AoPWV directly from the analysis of a pulse signal without a need for information about age, sex, height, weight or other factors. These systems or methods may be used to monitor blood pressure in a continual fashion and to assess aortic stiffness for health risk estimation.

In the embodiments described herein, AoPWV may be determined from a pulse signal acquired from the exterior of an individual's body. Generally, pulse signals include three wave components: a primary wave, a reflected wave and a dicrotic wave. Analysis of these components can be used to determine the AoPWV.

The aortic reflected wave is a wave that originates in the aorta and other blood vessels distal to the aorta. Each cardiac contraction initiates a primary wave that travels down the walls of the aorta. Reflections of the primary wave are generated and return towards the heart in response to various reflecting sites. Reflecting sites can include, but are not limited to, sites where the aorta gives rise to other blood vessels (e.g. renal arteries), where the aorta narrows, where the aorta wall properties vary, where the aorta bifurcates to form the iliac arteries and various other reflecting sites that may occur, such as in response to a range of phenomena associated with the distal arterial tree, for example. Reflections occurring at a number of separate sites can sum to form a reflected wave that may be detectable in an arterial pulse signal acquired from a suitable location.

An arterial pulse signal can be acquired non-invasively using a variety of techniques. In many cases, pulse sensors placed on, or superior to, an individual's lower abdomen are able to acquire the pulse signal in a way that allows identification of an aortic reflected wave component of the pulse signal. Examples of suitable locations for non-invasive arterial pulse sensors include placement on the trunk, upper extremities and head of an individual although other suitable locations may also be used. Suitable sensor locations generally refer to sensor locations that allow acquisition of the pulse signal such that a reflected wave component of the pulse signal is present in the sensed data and allows characterization of reflected wave onset.

In some cases, suitable locations may be identified by analyzing the pulse signals received from the pulse sensors. In some cases, the pulse signal may be analyzed to determine that it has a sufficient signal to noise ratio and contains signal components corresponding to the primary wave, the reflected wave and the dicrotic wave. For example, the received pulse signals may be compared to error condition thresholds. If the pulse signals satisfy the error condition thresholds (i.e. if the pulse signals are not considered erroneous or invalid based on the set thresholds) then the location may be identified as being a suitable location for identifying the individual's AoPWV.

In various embodiments described in accordance with the teachings herein, an individual's AoPWV can be identified from an arterial pulse signal. Once the pulse signal has been acquired, signal analysis techniques can be applied in order to derive AoPWV. In various embodiments described herein, derivatives of the pulse signal may be analyzed in order to derive the AoPWV. In some cases, analysis of pulse signal derivatives can reveal subtle wave components.

In some cases, polynomial smoothing methods may be used to smooth a received pulse signal and obtain derivatives of the pulse signal. For example, the Savitzky-Golay method of polynomial curve fitting can be used in some embodiments to determine and smooth pulse signal derivatives while retaining high frequency content. Various alternative polynomial smoothing techniques may be used, such as spline interpolation for example.

In some embodiments described herein, the first and third derivatives of the pulse signal may be used to identify primary and reflected waves for derivation of the AoPWV. For example, the second peak of the third derivative may be used to identify a reflected wave onset point in the pulse signal. The second peak may then be used to identify a corresponding point in the first derivative signal. This point may be referred to as the reflected wave onset point (RWOP) or the first derivative onset point. In some cases, the fourth derivative of the pulse signal may be used to identify an onset point test window for examining the third derivative. A first window peak of the third derivative in the onset point test window may then be used to identify the reflected wave onset point.

In some embodiments, the RWOP may be used to determine a reflected wave ratio. The reflected wave ratio may be determined using a normalized height of the RWOP. The reflected wave ratio may then be used to determine the individual's AoPWV. In some cases, the individual's AoPWV may then be compared to population averages to identify the individual's physiological age and/or may be used to determine the individual's blood pressure.

The example embodiments of the systems and methods described herein may be implemented as a combination of hardware or software. In some cases, the example embodiments described herein may be implemented, at least in part, by using one or more computer programs, executing on one or more programmable devices having at least one processing element, and a data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Referring now to FIG. 1, shown therein is a block diagram of an example embodiment of a system 10 that can be used to monitor aortic pulse velocity and blood pressure for an individual. The system 10 includes an operator unit 12, a data acquisition unit 40, and a sensor unit 42. The system 10 is provided as an example and there can be other embodiments of the system 10 with different components or a different configuration of the components described herein. The system 10 further includes several power supplies (not all shown) connected to various components of the system 10 for providing power thereto as is commonly known to those skilled in the art. In general, a user may interact with the operator unit 12 to acquire pulse signals from a sensor unit 42 located on the exterior of an individual, to perform pulse signal analysis and review the results of the analysis.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30, various programs 32, a data acquisition interface 34, a data analyzer 36, and one or more databases 38. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power processor depending on the configuration, purposes and requirements of the system 10 as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

Figure 5:
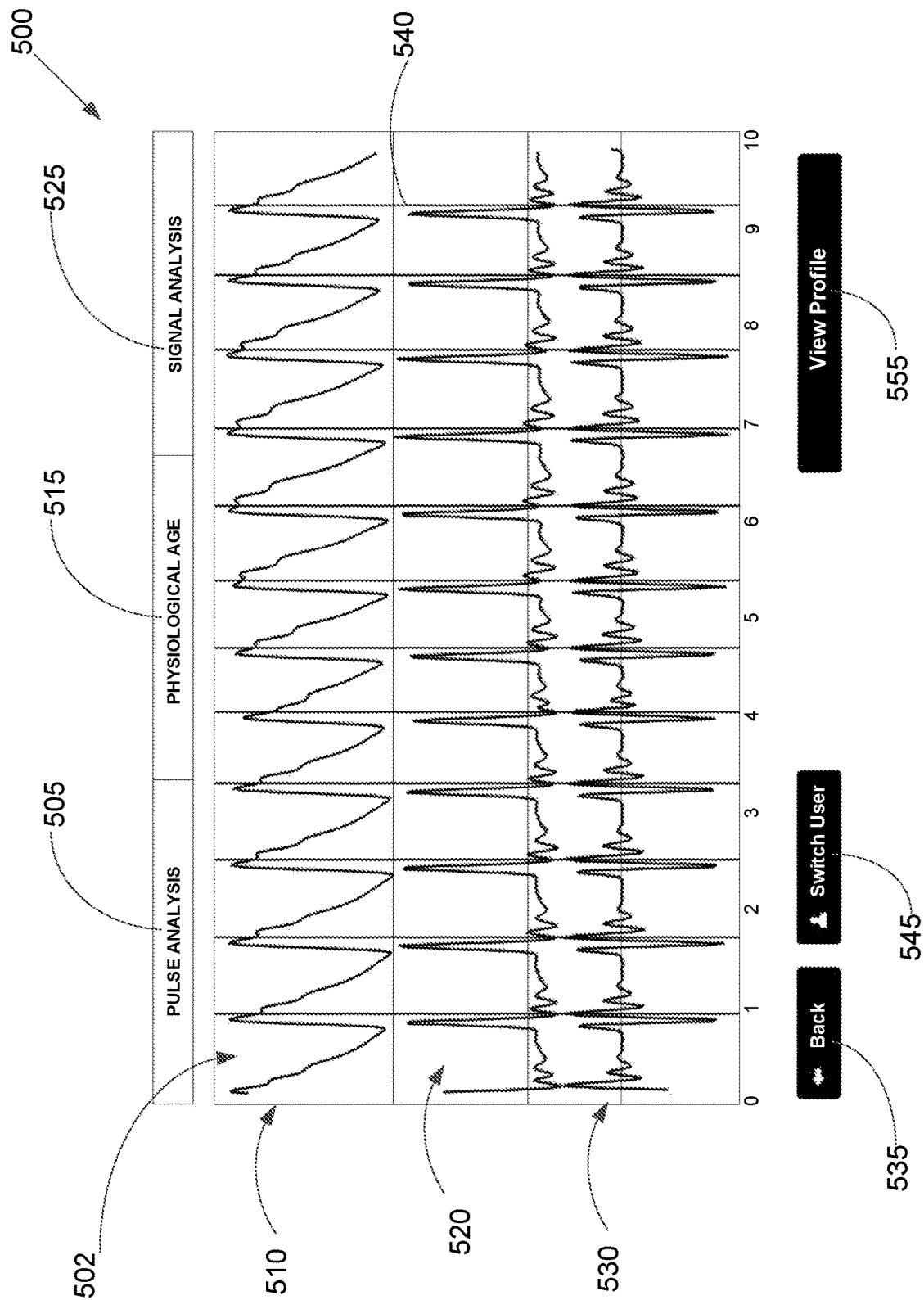
FIG. 5 is a screenshot of an example embodiment of a graphical user interface (GUI) showing a plot of a pulse signal, the first derivative of the pulse signal and the third derivative of the pulse signal.
Figure 7A:
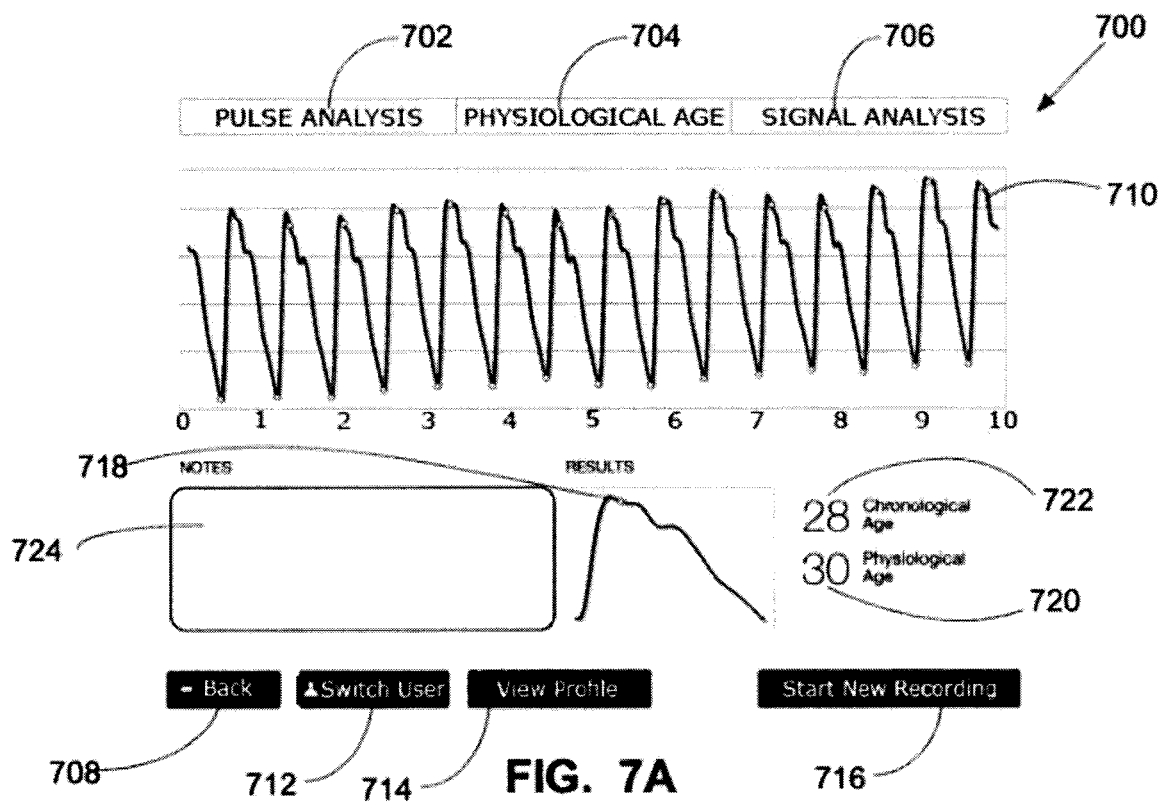
FIG. 7A is a screenshot of an example embodiment of a GUI that may be presented to a user of the system.
Figure 7B:
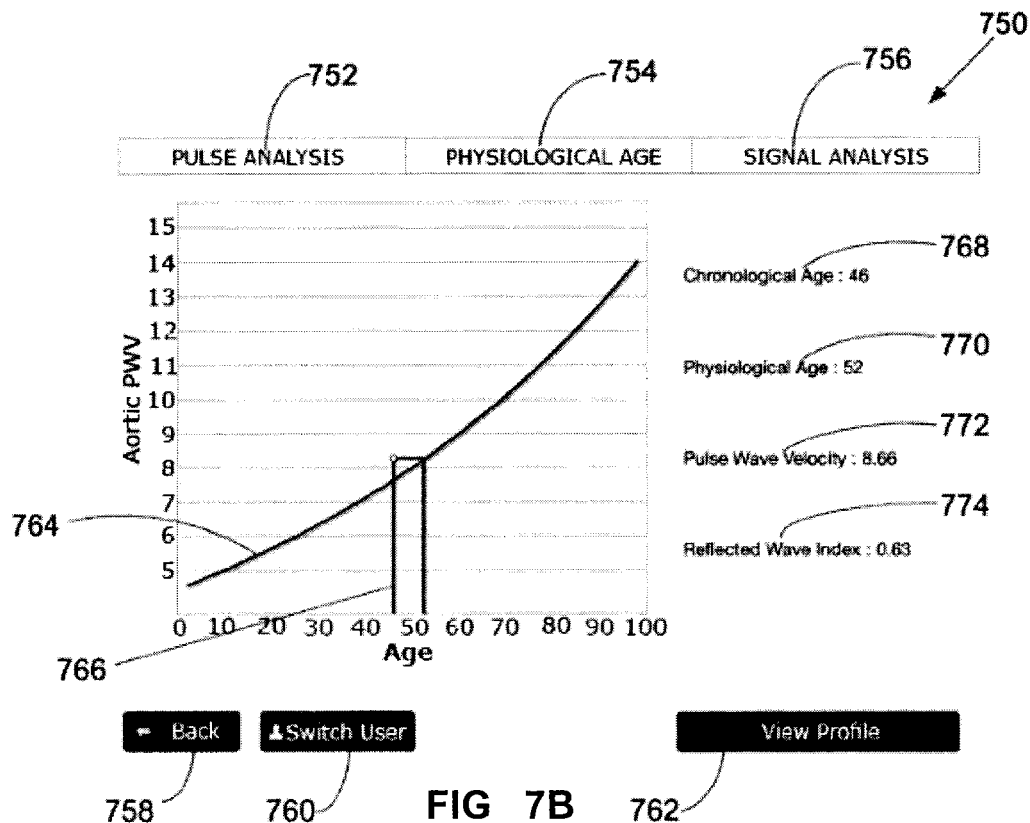
FIG. 7B is a diagram illustrating another example screenshot of a GUI that may be presented to a user of the system to display cardiac information for an individual being tested.

The display 16 may be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or handheld device such as an LCD-based display and the like. Examples of GUIs that may be shown to a user on the display 16 are shown in FIGS. 5, 7A and 7B.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or computers. In some cases, the interface unit 20 can include at least one of a serial port, a parallel port or a USB port that provides USB connectivity. The interface unit 20 can also include at least one of an Internet, a Local Area Network (LAN), an Ethernet, a Firewire, a modem or a digital subscriber line connection. In some embodiments, various combinations of these elements may be incorporated within the interface unit 20.

The I/O hardware 22 is optional and can include, but is not limited to, at least one of a microphone, a speaker and a printer, for example, depending on the configuration of the operator unit 12.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 may include RAM, ROM, one or more hard drives, one or more flash drives or some other suitable data storage elements such as disk drives, etc. The memory unit 28 may be used to store an operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, viewing and manipulating data, adjusting parameters for data analysis as well as sending messages as the case may be.

The data acquisition interface 34 may be used to obtain or record pulse signals that are sensed by the sensor unit 42. The data acquisition interface 34 is coupled to the data acquisition unit 40 and the sensor unit 42 in order to acquire these signals. In some cases, the data acquisition interface 34 may be integrated into the data acquisition unit 40 as a software or hardware component operating in conjunction with the data acquisition unit 40.

The data acquisition unit 40 may be used to control the operation of sensor unit 42 and to transfer pulse signals to the operator unit 12 through the interface unit 20. In some embodiments, the data acquisition unit 40 and the sensor unit 42 may be combined as a single unit, while in other embodiments they may operate as separate units. In some cases, the data acquisition unit 40, the sensor unit 42 and the operator unit 12 can be combined as a single unit. In some cases, the data acquisition unit 40 and sensor unit 42 may be wireless devices that are wirelessly coupled to the operator unit 12 and each (or a combined unit) may include a battery or other power source.

It should be noted that the data acquisition interface 34 may also obtain pulse signal data that is stored on a data store, such as the databases 28 or an external data store, or received from another computing device via the interface unit 20 or the wireless unit 24, for example, rather than obtain the pulse signal data by using the data acquisition unit 40 and the sensor unit 42. In other words, there may be cases in which the data acquisition interface 34 may obtain pre-recorded pulse signal data for analysis by the data analyzer 36.

The data analyzer 36 may be configured to process the pulse signal data that was obtained by the data acquisition interface 34 in order to monitor an individual's aortic pulse wave velocity. In at least some embodiments, the data analyzer 36 may be further operable to process the pulse signal data to monitor an individual's blood pressure and/or to provide an estimated physiological age.

The data analyzer 36 may also process the pulse signal data to determine whether the acquired signals satisfy error condition thresholds. Such error processing may be used to determine whether the sensor unit 42 has been placed at a suitable location for identifying the individual's aortic pulse wave velocity. Example embodiments of analysis methods that may be employed by the data analyzer 36 are described in more detail with respect to FIGS. 2, 3 and 8.

In alternative embodiments, the data acquisition interface 34 and data analyzer 36 may be combined as a single hardware and software component or may be separated into multiple hardware and software components. The data acquisition interface 34 and data analyzer 36 are typically implemented using software, but there may be instances in which they may be implemented using FPGA or application specific circuitry.

For ease of understanding, certain aspects of the methods described herein are described as being performed by the data analyzer 36. It should be noted, however that these methods are not limited in that respect, and the various aspects of the methods described herein may be performed by other hardware and software components for determining AoPWV and other parameters.

The databases 38 may be used to store data for the system 10 such as system settings, parameter values, and calibration data. For example, in some embodiments, the system 10 may use initial calibration to determine the individual's blood pressure factors. In some cases, these blood pressure factors may be stored in databases 38 and used in various methods described herein to determine the individual's blood pressure using their aortic pulse wave velocity. The databases 38 may also store other information that is used for the operation of the programs 32 or the operating system 30 such as dynamically linked libraries and the like.

The operator unit 12 comprises at least one interface that the processing unit 14 communicates with in order to receive or send information. This interface may be the user interface 18, the interface unit 20 or the wireless unit 24, depending on the particular configuration of the operator unit 12. For example, the blood pressure factors used by the system 10 in order to monitor blood pressure using AoPWV may be inputted by a user through the user interface 18 or these blood pressure factors may be received through the interface unit 20 from a separate computing device or data store.

The processing unit 14 may communicate with either one of the user interface 18, the interface unit 20 or the wireless unit 24 as well as the display 16 or the I/O hardware 22 in order to output information related to at least one of the individual's AoPWV, blood pressure, the individual's 'physiological age', other information that may be derived from the pulse signals or system parameters.

Users of the operator unit 12 may communicate information across a network connection to a remote system for storage and/or further analysis in some embodiments. This communication may also include email communication or other communication over a network such as the Internet or a wireless cellular network, for example.

In some cases, the user may also use the operator unit 12 to input information for system parameters that are used for proper operation of the system 10 such as calibration information and other system operating parameters as is known by those skilled in the art. Data that are obtained from tests, as well as parameters used for operation of the system 10, may be stored in the memory unit 28. The stored data may include raw recorded data as well as processed signal data.

The data acquisition unit 40 comprises hardware and circuitry that may be used to record pulse signals from an individual. The sensor unit 42 may be used to measure data and/or parameters that may be used to acquire a pulse signal from the individual.

In some embodiments, the sensor unit 42 may be an optical pulse sensor. Non-invasive optical pulse sensors can detect variations in light transmitted through or reflected from skin surfaces. In some embodiments, an optical sensor can be placed over an individual's fingernail to acquire a pulse signal. Other suitable sensor locations for an optical sensor may include, but are not limited to, the hypothenar area of the palm and the external auditory canal. A wide variety of other suitable locations may be used to acquire signals using an optical pulse sensor.

Various modifications can be made to the sensor unit 42. For example, light in the red, green or other wavelength regions may be effectively employed. In some embodiments, an optical pulse sensor can be operated in a transmission mode for illuminating elements on one side of the fingertip and in a reception mode for a photodetector element on the other side of the fingertip. Alternatively, in some embodiments, an optical pulse sensor may have an LED and a photodetector element that may be used in a reflective mode arrangement. In some cases, the photodetector element may be a phototransistor or a photodiode.

In some cases, a variety of alternative sensor instruments such as, but not limited to, a pressure tonometer, a piezo film, an impedance plethysmograph, or an inflatable cuff, for example, can be used as the sensor unit 42. Accordingly, the example methods for monitoring AoPWV described herein may be modified to account for differences in the pulse signals acquired by different sensor unit implementations. For example, the relationship of the reflected wave ratio to aortic pulse wave velocity may vary for different pulse acquisition sensors so different look-up tables may be necessary.

Suitable sensor locations may also vary for differing sensor instruments. For example, a pressure sensor may use a physically pulsatile arterial pulse signal for adequate operation. Furthermore, in some cases the sensor location may affect the morphology of the acquired pulse signal. Accordingly, the pulse detection methods may need to be modified in certain cases to account for these changes in morphology to obtain a reflected wave ratio that can be calibrated with the aortic pulse wave velocity.

In some cases, in order to obtain sufficient signal detail for pulse signal analysis the optical sensor samples the pulse signal with sufficient sampling speed and resolution. For example, a 200 Hz sampling speed with 20 bits of resolution may be used in some embodiments. In some cases, the data acquisition unit 40 can adjust the sampling speed and sampling resolution of an Analog to Digital convertor (ADC) associated with the sensor unit 42.

In some cases, the sensor unit 42 and the data acquisition unit 40 can be combined in a single unit. For example, in one embodiment, an optical pulse sensor such as an oximeter incorporating an infrared LED, with a wavelength of 880 nm and a matching photodiode, may operate in transmission mode when placed over a finger of the individual. The oximeter may have onboard processing circuitry (i.e. the data acquisition unit 40) that acquires the pulse signal using an analog-to-digital conversion (ADC) at the desired sampling speed and resolution.

The data acquisition unit 40 may be coupled to the operator unit 12 using various interfaces as described above. The data acquisition unit 40 may send data that has been measured from the individual to the operator unit 12 such as, but not limited to, at least one of pulse signal data, heart rate data, oxygen saturation data, and battery voltage data, for example. In some cases, the data may be encoded so as to ensure that missed data can be detected. For example, where a 20 bit pulse sample is used, the data acquisition unit 40 may assign a number from 0 to 255 to each 20 bit pulse sample. The data acquisition interface 34 can extract 20 bit pulse samples and ensure that the 0 to 255 assigned numbers are incrementing in a way that indicates no missed data. In some cases, if there is missed data then the missed data can be replaced with an average of the samples immediately before and after the missed data. The data acquisition interface 34 can combine the received samples into a continuous data sample for analysis.

In some embodiments, the pulse signal may be acquired without using any signal conditioning techniques. In some cases, conditioning the acquired signal may affect the pulse signal in ways that make analysis of primary and reflected wave components less effective.

Figure 2:
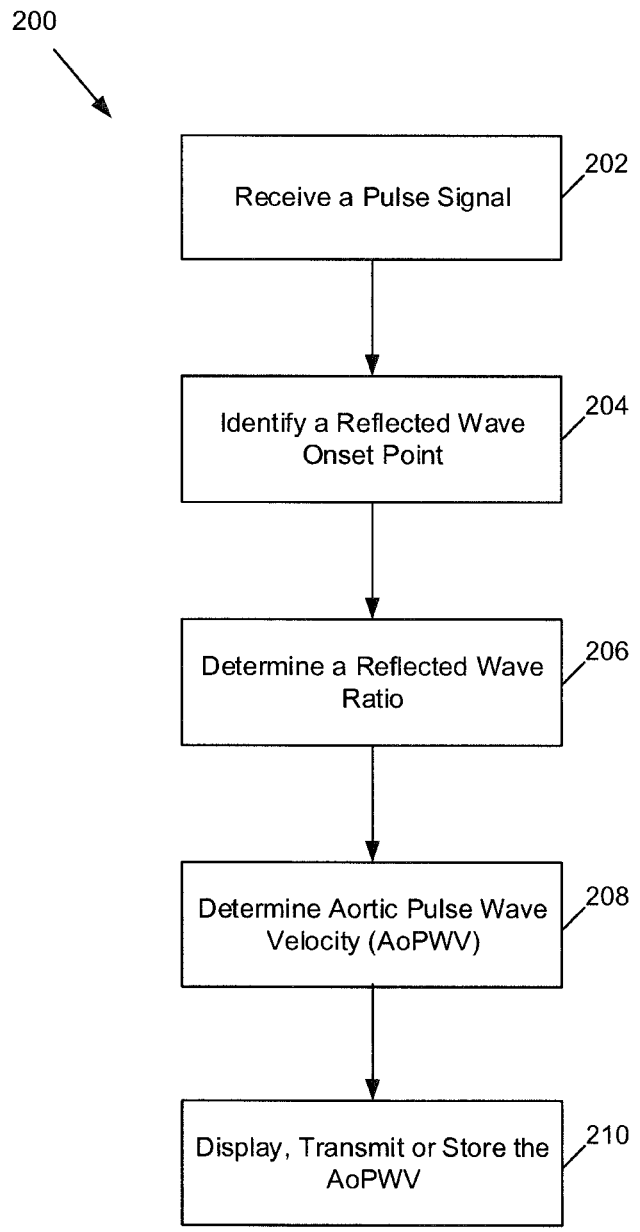
FIG. 2 is a flowchart of an example embodiment of a method for monitoring aortic pulse wave velocity.

Referring now to FIG. 2, shown therein is flowchart of an example embodiment of a method 200 for monitoring aortic pulse wave velocity. Method 200 can be used by the system 10 to monitor the aortic pulse wave velocity of an individual.

At 202, data analyzer 36 receives a pulse signal. The pulse signal may be received from a sensor unit 42 positioned on the exterior of an individual's body. The sensor unit 42 can be positioned at a sensor location that allows acquisition of the pulse signal such that a reflected wave component of the pulse signal is present and allows characterization of reflected wave onset. In some embodiments, the data analyzer 36 may receive a pulse signal that has been pre-recorded and stored in a data store, as described previously.

In some embodiments the sensor unit 42 and the data acquisition unit 40 may be combined into a pulse acquisition unit. In such embodiments, the pulse acquisition unit may be configured to acquire the pulse signal from the individual and to process the signal or transmit the signal to a pulse analysis unit for processing. In some embodiments, the pulse acquisition unit may further incorporate the pulse analysis unit. In other embodiments, the operator unit 12 or another processing unit may operate as the pulse analysis unit.

In some cases, the data analyzer 36 may determine if the pulse signal satisfies at least one error threshold condition prior to identifying a RWOP. In some cases, determining if the pulse signal satisfies the error threshold condition may also be used to determine if the sensor unit 42 has been placed in a suitable sensor location for acquiring the pulse signal according to method 200. An example method for determining if a pulse signal satisfies error threshold conditions will be described in further detail below with reference to FIG. 8.

Depending on the type of sensor unit 42 used, the pulse signal may be acquired in different forms. For example, in some embodiments the pulse signal can be acquired as a volume pulse signal and the data analyzer 36 may analyze the volume pulse signal directly. In other cases, the data analyzer 36 may convert or transform the volume pulse signal into a pressure pulse signal prior to performing data analysis including identifying a RWOP. An example derivation of a transfer function that may be used is described in the article 'Noninvasive Assessment of the Digital Volume Pulse: Comparison with the Peripheral Pressure Pulse' by Millasseau et al (Hypertension, 2000; 36:952-956), the entirety of which is hereby incorporated by reference.

In some embodiments, the pulse signal may be filtered by the data acquisition interface 34 or the data analyzer 36 prior to being processed by the data analyzer 36. For example, the acquired pulse signal may be filtered to remove noise or other unwanted artifacts. An example of this is using a Finite Impulse Response (FIR) filter to remove high frequency noise as well as other unwanted signal components, such as signal components due to respiratory variations. For instance, the FIR filter may have a 200th-order pass band, allowing signal components of the pulse signal for frequencies between 0.4-40 Hz to pass, while blocking other signal components. Other appropriate filtering techniques may also be used.

At 204 the data analyzer 36 can identify a RWOP in the pulse signal. In some cases, the data analyzer 36 may identify the RWOP (and the reflected wave ratio) using derivatives of the pulse signal. Various methods may be used to determine pulse signal derivatives, in some cases along with smoothing techniques to generate smoothed derivative signals such as, but not limited to, a Savitzky-Golay technique may be used to determine smooth pulse signal derivatives, for example.

In some embodiments, the data analyzer 36 may determine first, second, third and fourth derivatives of the pulse signal. A smoothing window may be applied to the pulse signal to smooth the determined derivatives by, for each data point in the acquired pulse signal, smoothing the determined derivatives using adjacent points within the smoothing window. For instance, the smoothing window may take into account a set of data points before and a set of data points after each data point, e.g. 4 points before and after, 6 points before and after etc.

The data analyzer 36 may then determine a pulse onset point for each heartbeat pulse in the pulse signal using the determined derivatives. For example, the data analyzer 36 may process the first derivative to identify local signals maximums and minimums in the acquired pulse signal. Signal minimums in the pulse signal may be determined as zero crossing points of the first derivative from negative to positive, while signal maximums may be determined as zero crossing points of the first derivative from positive to negative. Similarly, this methodology may be used to identify local maximums and minimums in the first derivative by analyzing the second derivative and so forth for the third and fourth derivatives.

The pulse onset point for each pulse may be determined by identifying a first local maximum in the first derivative. A pulse onset test window may be used to validate the first local maximum in the first derivative. The pulse onset test window may be determined based on the heart rate, e.g. as a portion of a heartbeat, such as half a beat length in time. Then, analyzing the first derivative backwards in time from the first local maximum in the first derivative, the first local minimum of the pulse signal can be identified. The first local minimum may be determined to be the pulse onset point for a particular heartbeat wave pulse.

The local maximums of the pulse signal may then be identified using the first derivative. This time, analyzing the first derivative forward in time from the first local maximum in the first derivative, the local maximums of the pulse signal can be identified by the zero crossings (from positive to negative). Once again, the local maximums of the pulse signal can be confirmed using a local max test window determined based on the heart rate, typically shorter than the pulse onset test window (e.g. as ⅓ or ¼ of a heartbeat length).

In some embodiments, the third derivative and fourth derivative may be used to identify the reflected wave onset point. The fourth derivative can be used to identify an onset point test window that can be applied to the third derivative to identify the reflected wave onset point in the third derivative. A first peak of the third derivative within the onset point test window (a first window peak) can be identified. This first window peak (i.e. the point in time corresponding to the first window peak) may be identified as the reflected wave onset point.

For each pulse, a first local maximum (a first peak), second local maximum (a second peak), and third local maximum (a third peak) can be identified in the fourth derivative. These local maximums or peaks may again be confirmed using a test window, e.g. +/−0.05 s. The third peak location can be used to define the onset point test window.

The local maxima in the fourth derivative may be identified by analyzing the fourth derivative starting from the onset of each pulse (determined as described above). From the point in the fourth derivative corresponding to the onset point, and moving backwards in time, the fourth derivative can be analyzed until a zero crossing from positive to negative is identified (as the analysis is moving backwards in time, this will be the case where if t<t+1, f''''(t)<0 and f''''(t+1)>=0). From this zero crossing, the first three "peaks" (or local maxima) in the 4th derivative are identified.

In some cases, at least one of the peaks in the $4^{th}$ derivative of a pulse may occur prior to the onset point for that pulse identified above. This may occur depending on the remaining blood pressure from a previous pulse.

The first, second and third peak may be used to determine if the acquired pulse signal satisfies error conditions, as will be discussed further below. In some cases, if the acquired pulse signal does not satisfy the error conditions, then the pulse signal may not be usable for determining the reflected wave ratio.

In some embodiments, the reflected wave onset point may be identified beginning from a location in the third derivative corresponding to the third peak location and identifying the next closest local maximum (moving forward in time). This next closest local maximum may be determined to be the reflected wave onset point (RWOP).

In some embodiments, the reflected wave onset point for a particular pulse may be identified in the third derivative. A local minimum of the third derivative for that particular pulse can be identified. Beginning from the local minimum, and moving forward in time, the reflected wave onset point (RWOP) may be identified as the next location t in the third derivative where t<t+1 and f'''(t)>=f'''(t+1). That is, the next peak in the third derivative (beginning from the local minimum and moving forward in time) may be identified as the RWOP.

Another example of a method using pulse signal derivatives to identify the RWOP and reflected wave ratio will be described in further detail below with regards to FIG. 3.

At 206, the data analyzer 36 can determine a reflected wave ratio at the RWOP. In accordance with the teachings herein, an individual's reflected wave ratio has been identified as having a generally linear relationship with age. An individual's reflected wave ratio can also be used to determine AoPWV. An example plot illustrating reflected wave ratios compared with age is described below with reference to FIG. 6.

At 208, the data analyzer 36 determines the aortic pulse wave velocity from the reflected wave ratio. In some cases, the aortic pulse wave velocity can be determined from the reflected wave ratio using a look-up table. The look-up table may include a mapping of reflected wave ratios to aortic pulse wave velocity.

In some cases, the look-up table may be determined experimentally. In some cases, the look-up table provides a value that is an average of many experimental observations. For example, AoPWV can be derived using the 'gold standard' carotid-femoral testing procedure simultaneously with acquisition of the reflected wave ratio. This data can be used to map reflected wave ratio values to AoPWV values.

At 210, the system 10 may perform various actions with the determined aortic pulse wave velocity. In some cases, the AoPWV can be displayed on the display 16. For example, the display 16 may display the aortic pulse wave velocity in a GUI such as that shown in FIG. 8B, discussed below. Various other values derived from analysis of the pulse signal may also be displayed on the display 16. Alternatively, or in addition thereto, the derived values may be transmitted to another electronic device. Alternatively, or in addition thereto, the derived values may be stored in a data store.

The data analyzer 36 may also transmit the aortic pulse wave velocity to a remote location for storage or further analysis. For example, the aortic pulse wave velocity may be transmitted over the internet to be stored in a profile for the individual in a computer system or database. The individual may be able to access their profile over the internet to review the changes in their AoPWV over time. This may also allow the individual to share information about their AoPWV with other individuals such as a health or fitness professional.

In some cases, the data analyzer 36 may store the AoPWV in the databases 38. The AoPWV may be stored for further analysis at a later time, for later transmission, for display to the user at a later time or for various other uses.

In some cases, the data analyzer 36 may perform further analysis on the AoPWV. In some cases, an individual's heart rate may affect their AoPWV. For example, a 50% increase in heart rate above 60 beats per minute ("bpm") may result in a ~5% increase in AoPWV. Similarly, each 1% increase in heart rate above 60 bpm may result in a ~0.1% increase in AoPWV. Accordingly, it may be desirable to normalize the AoPWV determined by the data analyzer 36 to account for the individual's current heart rate.

In some cases, the pulse signal received by the data analyzer 36 may include information related to the individual's current heart rate. In such cases, the data analyzer 36 may use the heart rate information from the pulse signal to determine a normalized aortic pulse wave velocity. For example, the data analyzer 36 may normalize AoPWV using a baseline heart rate of the individual's resting heart rate or an estimated resting heart rate or baseline heart rate range. For example, in some cases AoPWV may be normalized to a heart rate of 60 bpm. An example formula for determining a normalized AoPWV is shown below:

Let HR>60=the number of bpm that the heart rate is above 60 bpm. If the heart rate is equal to or less than 60 bpm then HR>60=0

Let HR>60/60×100=% HR>60

AoPWV normalized to 60 bpm=$AoPWV_{60}$ $AoPWV_{60}$=AoPWV−AoPWV(% HR>60×0.1)

In some cases, the heart rate information received from the pulse signal may be used to normalize the reflected wave ratio prior to determining the AoPWV. The normalized reflected wave ratio can then be used to determine the AoPWV. An example of normalizing the reflected wave ratio using heart rate information will be described below with reference to FIG. 10.

In some cases, the data analyzer 36 may also determine an individual's blood pressure using the AoPWV. In some cases, the normalized AoPWV may also be used to determine the individual's blood pressure.

In at least some cases, the data analyzer 36 may also calibrate blood pressure factors for the individual. The data analyzer 36 can then determine the individual's blood pressure using the aortic pulse wave velocity and the blood pressure factors. The blood pressure factors may be determined during an initial calibration process and may then be used on a continual basis by the data analyzer 36 to monitor the individual's blood pressure. In some cases, the blood pressure factors may need to be re-calibrated at intervals after the initial calibration.

A relationship between pulse wave velocity and blood pressure was identified by Theodor et al. in their article 'Implantable Acceleration Plethysmography for Blood Pressure Determination' (35th Annual International Conference of the IEEE EMBS), the entirety of which is hereby incorporated by reference. Pulse wave velocity and blood pressure can be related using equation (1):

$$BP=m_{BP}*PWV^2+c_{BP} \quad (1)$$

Equation 1 indicates that the relationship between AoPWV and blood pressure (in Equation (1) BP refers to systolic blood pressure) is nonlinear. Equation (1) uses an empirical slope mBP and offset cBP—both parameters depend on individual characteristics of the patient. Accordingly, the blood pressure factors $m_{BP}$ and $c_{BP}$ must be determined for an individual prior to being able to determining blood pressure using AoPWV. The blood pressure factors $m_{BP}$ and $c_{BP}$ may be used to determine the slope and offset of the linear relationship between AoPWV and blood pressure.

To determine the blood pressure factors, two different blood pressure readings may be taken. This may be done by having the individual take an initial blood pressure reading using an oscillometric BP cuff while seated and a second reading after standing up. Capturing the specific beat when the blood pressure is taken sitting and then standing up will allow AoPWV readings to be matched to associated blood pressure readings for the two instances. Once the blood pressure factors have been determined, AoPWV can be used for continual monitoring of blood pressure using the various methods described herein. This may allow an individual's blood pressure to be monitored on a continual and ongoing basis using a single external sensor.

Figure 3:
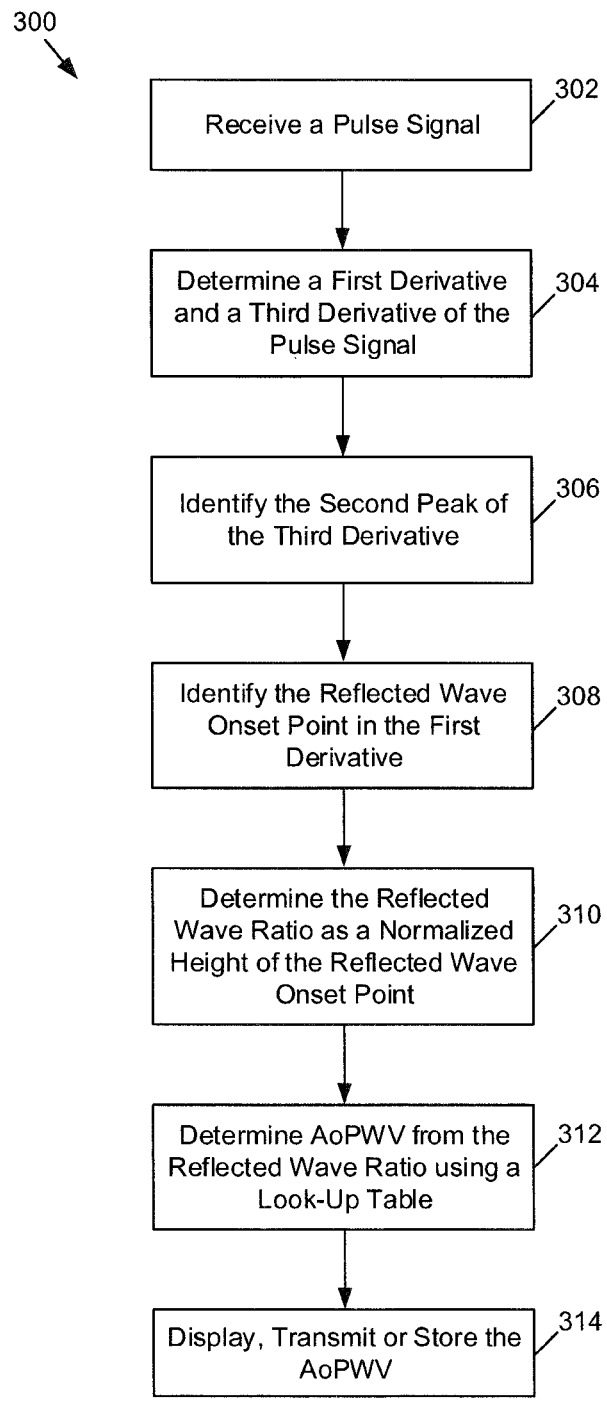
FIG. 3 is a flowchart of another example embodiment of a method for monitoring aortic pulse wave velocity.

Referring now to FIG. 3, shown therein is flowchart of an example embodiment of a method 300 for monitoring aortic pulse wave velocity that may be implemented using the system 10.

At 302, the data analyzer 36 receives a pulse signal. As mentioned above, in some cases the pulse signal may be a volume pulse signal and the data analyzer 36 may analyze the volume pulse signal directly. In other cases, the data analyzer 36 may convert the volume pulse signal to a pressure pulse signal before performing the analysis.

At 304, the data analyzer 36 may determine a first derivative and a third derivative from the pulse signal. Various signal analysis techniques may be used to determine the first derivative and the third derivative. For example, the pulse signal may be processed using the Savitzky-Golay polynomial smoothing/differentiation filter method to generate a smoothed version of the pulse signal derivatives of the pulse signal. In some embodiments, the data analyzer 36 may use the first derivative and the third derivative to identify the RWOP in the pulse signal.

At 306, the data analyzer 36 may identify the second peak of the third derivative. The data analyzer 36 may be able to automatically identify the second peak of the third derivative using various peak detection methods. For example, the second positive to negative zero crossing of the 4th derivative may be used to detect the second peak of the third derivative.

At 308, the data analyzer 36 identifies the RWOP in the first derivative using the second peak of the third derivative. The RWOP may be identified as the point in the first derivative corresponding to the second peak of the third derivative. In some cases, this point may be referred to as the first derivative onset point. An example of a GUI illustrating the relationship between an acquired pulse signal, first derivative, and third derivative is described below with reference to FIG. 5.

Referring again to FIG. 3, at 310 the data analyzer 36 may determine the reflected wave ratio as a normalized height of the first derivative onset point.

In some embodiments, the data analyzer 36 may identify a first peak in the first derivative. For example, the first peak may be the point of maximum amplitude in the test window for the pulse signal. The data analyzer 36 may then measure a height of the first peak. The data analyzer 36 may normalize the first derivative based on the height of the first peak. The data analyzer 36 may measure a height of the normalized first derivative at the first derivative onset point to determine the reflected wave ratio.

For example, the height of the first peak of the first derivative may be added to the amplitude of every point in the first derivative. The first peak of the first derivative may then be normalized to a value of 1. As a result of this example normalization, a point that originally was located on the zero axis will have a normalized height of 0.50. The normalized height of the RWOP (i.e. the reflected wave ratio in this embodiment) may be determined by measuring a height of the normalized first derivative at the first derivative onset point. Using this normalization approach, the reflected wave ratio has a value that ranges between 0 and 1. In some cases, normalized height of the RWOP may be determined as:

$$RWOP_{normalized} = \frac{M + R}{2M}$$

where M is the height of the first peak, and R is the height of the RWOP.

At 312, the data analyzer 36 may determine the AoPWV from the reflected wave ratio using a look-up table as described previously for method 200.

At 314, the system 10 may perform at least one of storing, transmitting and displaying the AoPWV. These acts may be performed in the same manner as described above with respect to FIG. 2 at 210.

Figure 4:
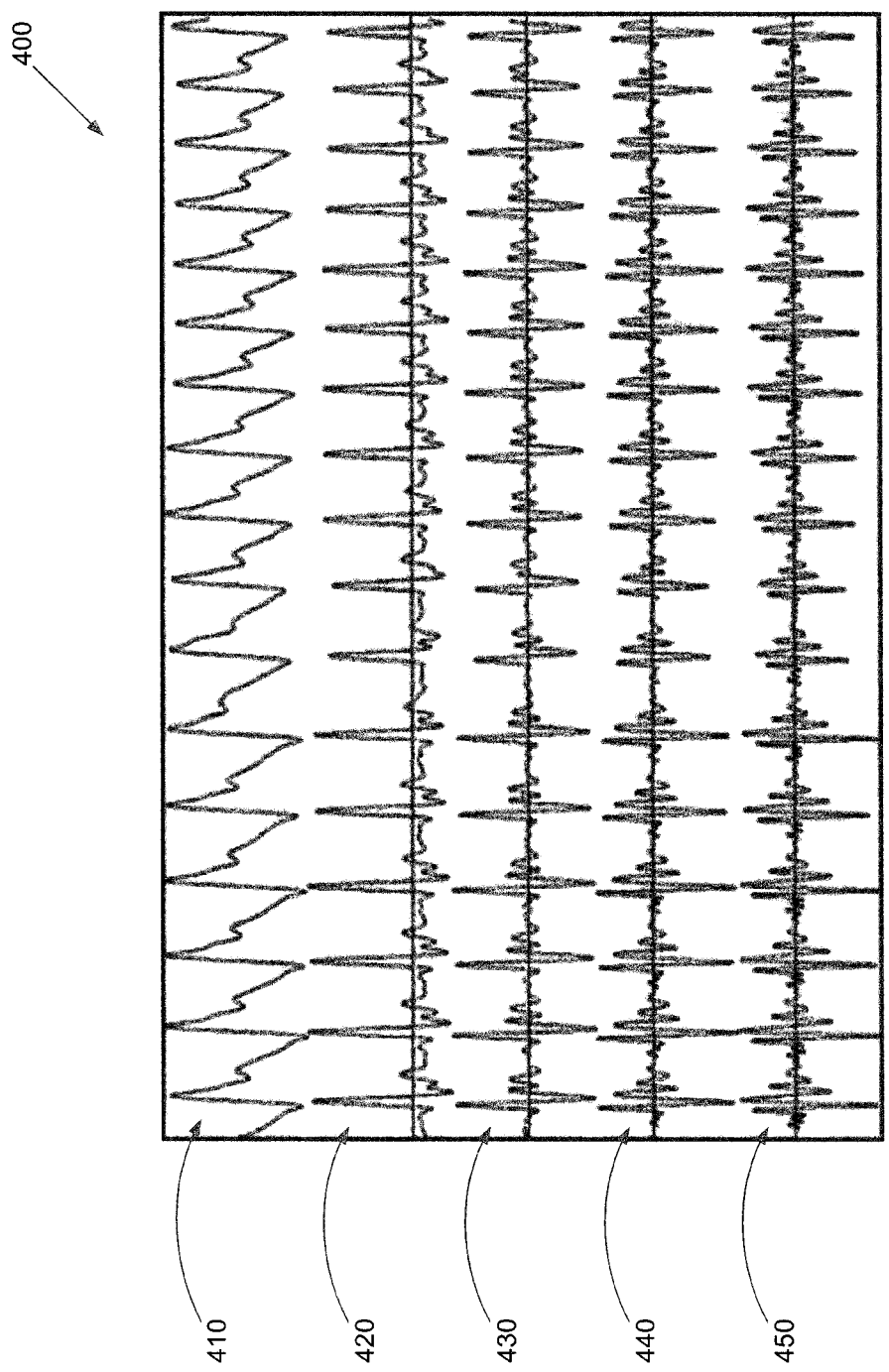
FIG. 4 is a diagram illustrating an example pulse signal and derivatives of the pulse signal.

Referring now to FIG. 4, shown therein is a diagram illustrating an example plot 400 of a volume pulse signal 410 and the first derivative 420, the second derivative 430, the third derivative 440, and the fourth derivative 450 of the pulse signal 410. The plot 400 shows time represented in second on the x-axis and signal amplitude that has been re-scaled to have values between 0 and 1 on the y-axis. The signal amplitude for the volume pulse signal 410 may be derived from a voltage reading of the sensor unit 42 in Volts, while the signal amplitude for the first derivative 420, the second derivative 430, the third derivative 440, and the fourth derivative 450 are derivatives of the signal amplitude of the volume pulse signal 410. Various signal processing techniques apparent to those skilled in the art may be used to determine the derivatives of the pulse signal. For example, the Savitzky-Golay method of polynomial smoothing and analysis may be used in some embodiments.

As mentioned above, various embodiments of the systems and methods described in accordance with the teachings herein may analyze the derivatives of the pulse signal to identify subtle wave components and other signal parameters. For example, the first derivative 420 and the third derivative 440 may be used to identify the RWOP and determine the reflected wave ratio. In some cases, the fourth derivative 450 may be used to determine whether the pulse signal 410 satisfies an error threshold condition.

Referring now to FIG. 5, shown therein is an example GUI 500 that may be displayed to a user who is using the system 10. The GUI 500 may be an example of a Pulse Analysis screen that can be shown to a user. The GUI 500 includes navigational buttons such as at least one of a pulse analysis button 505, a physiological age button 515, a signal analysis button 525, a back button 535, a switch user button 545 and a view profile button 555. The various navigational buttons may be operated by a user using the user interface 18 to navigate among various GUI screens of the system 10. The GUI 500 also shows a plot 502 showing the pulse signal 510, the first derivative 520 and the third derivative 530. Plot 502 shows time on the x-axis in seconds and signal ampli-tude on the y-axis. In plot 502, the second peak of the third derivative 530 has been identified for each pulse and is shown using RWOP line 540. The GUI 500 illustrates an example of the results of using the first and third derivatives to identify the RWOP line 540 in pulse signal 510.

Figure 6:
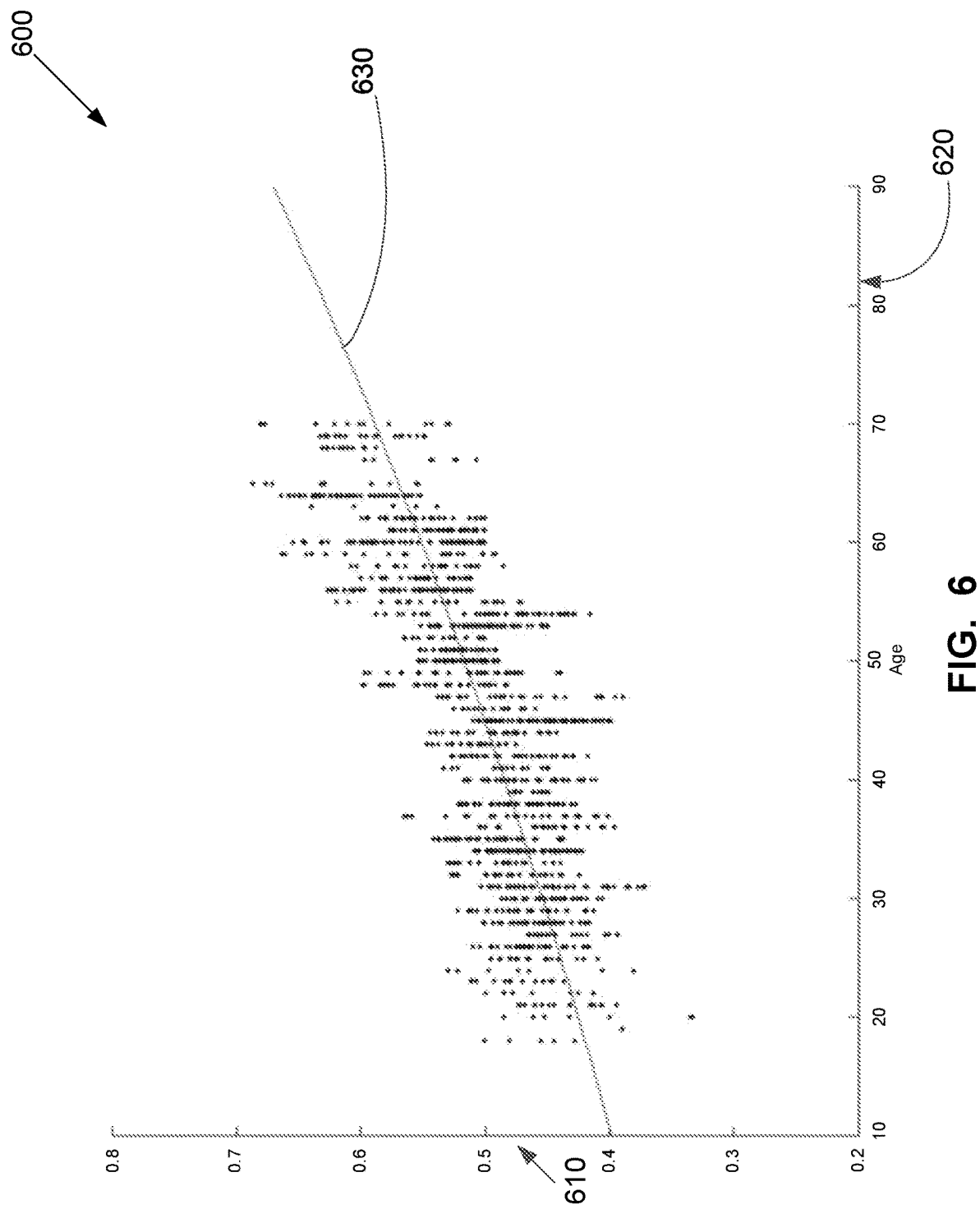
FIG. 6 is a diagram illustrating a plot of an example of reflected wave ratio against age.

Referring now to FIG. 6, shown therein is a diagram illustrating a plot 600 of a reflected wave ratio 610 on the y-axis compared with age 620 on the x-axis. Plot 600 represents data collected from a number of individuals over the age spectrum to identify a relationship between the reflected wave ratio 610 and age 620. Plot 600 shows a trend 630 of the reflected wave ratio 610 increasing with age 620 that is slightly exponential.

Referring now to FIG. 7A, shown therein is a screenshot of an example GUI 700 that may be presented to a user of the system 10. The GUI 700 is an example of a results page for an individual. The GUI 700 displays the pulse signal 710 acquired for the individual as well as various factors that may be determined through analysis of the pulse signal 710. The pulse signal 710 is shown on a graph where the x-axis represents time in seconds and the y-axis represents signal amplitude re-scaled to have values between 0 and 1.

As shown in the GUI 700, the RWOP 718 of the individual may be displayed along with their chronological age 722 and their physiological age 720. The physiological age 720 may be determined by comparing the AoPWV determined for that individual with a population average. The GUI 700 also includes a text box 724 allowing the user to input notes related to the results.

The GUI 700 includes a variety of navigational buttons that may be used to navigate among the different GUIs in the system 10. At least one of a pulse analysis button 702, a physiological age button 704, a signal analysis 706, a back button 708, a switch user button 712, and a view profile button 714 may be used to navigate through various GUIs in the system 10 to determine different values, display different information or input system parameters. A start new recording button 716 may be used to initiate the acquisition of a pulse signal from an individual using the sensor unit 42.

Referring now to FIG. 7B, shown therein is a screenshot of another example GUI 750 that may be displayed to a user of system 10. The GUI 750 displays a plot of average AoPWV 764 on the y-axis against population age on the x-axis. The individual's AoPWV 766 may be identified on the plot. A circle on the individual's AoPWV 766 indicates the individual's chronological age 768 on the plot. The intersection of the individual's AoPWV 766 and the average AoPWV 764 can be used to determine the individual's physiological age 770. The GUI 750 may also show numerical AoPWV values 772 and reflected wave index values (or ratio) 774.

The GUI 750 may also include a number of navigational buttons that can be used to navigate among the different GUIs in the system 10. At least one of a pulse analysis button 752, a physiological age button 754, a signal analysis 756, a back button 758, a switch user button 760, and a view profile button 762 may be used to navigate through various GUIs in the system 10 to determine different information, display different information or input system parameters.

Figure 8:
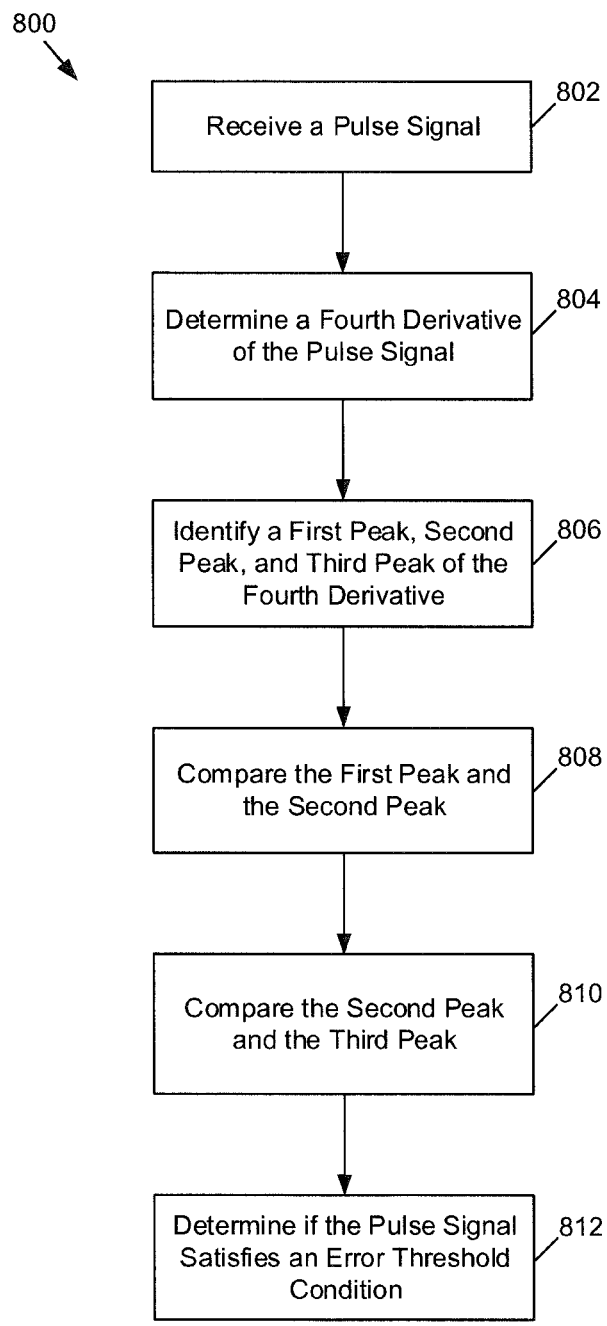
FIG. 8 is a flowchart of an example embodiment of a method for determining if a pulse signal satisfies error threshold conditions.

Referring now to FIG. 8, shown therein is an example embodiment of a method 800 for determining if a received pulse signal satisfies an error threshold condition. In some cases, the data analyzer 36 may determine if the pulse signal satisfies the error threshold condition prior to identifying the RWOP. In some cases, the data analyzer 36 may only perform at least one of the acts of identifying the RWOP, calculating the reflected wave ratio, and determining the aortic pulse wave velocity if the pulse signal satisfies the error threshold condition.

The method 800 may be used by the system 10 to eliminate poor quality pulses where the reflected wave cannot be identified with adequate accuracy. In some cases, the method 800 may also be used to identify suitable locations for the placement of sensor unit 42 on the exterior of an individual's body. For example, in some cases if less than 3 pulses satisfy the error threshold condition, the recording may need to be repeated or the sensor may need to be repositioned.

At 802, the data analyzer 36 receives a pulse signal. As mentioned above, in some cases the pulse signal may be a volume pulse signal. In some cases, the data analyzer 36 may convert the volume pulse signal to a pressure pulse signal. In some cases, the pulse signal may be obtained by the sensor unit and in other cases it may be prerecorded and obtained from a data store or a transmission from another device.

At 804, the data analyzer 36 determines a fourth derivative from the pulse signal. The fourth derivative may be determined using various analytical approaches such as the Savitzky-Golay method mentioned above.

At 806, the data analyzer 36 identifies a first peak, a second peak and a third peak from the fourth derivative of the pulse signal. The first, second and third peak may be identified automatically by the data analyzer 36 using various known peak detection methods. The first, second and third peak may be used to determine if the acquired pulse signal satisfies an error threshold condition.

The data analyzer 36 may determine if the first peak, second peak, and the third peak satisfy a plurality of peak error conditions. In some embodiments, the pulse signal may satisfy the error threshold condition if the first peak, second peak, and the third peak satisfy the plurality of peak error conditions.

In some embodiments, the plurality of peak error conditions may include a first threshold and a second threshold. In some embodiments, the plurality of peak error conditions may include an amplitude threshold, a first timing threshold, and a second timing threshold. The pulse signal may satisfy the error threshold condition if each of the amplitude threshold, the first timing threshold and the second timing threshold is satisfied.

The data analyzer 36 may compare the first peak and the second peak to determine if the second peak satisfies the amplitude threshold. For example, the height of the second peak may be a certain proportion of the height of the first peak (e.g. 80%) to satisfy the amplitude threshold.

The data analyzer 36 can also determine the distance between the first peak and the second peak (a first distance, e.g. in time) and the distance between the second peak and the third peak (a second distance). The first distance and second distance may then be compared to determine if the first timing threshold is satisfied. For example, the second distance may be limited to a maximum multiple of the first distance (e.g. 2 or 3). That is, the second distance may be less than three times the first distance to satisfy the first timing threshold. In other words, to satisfy the first timing threshold, the third peak may have occurred after the second peak but is spaced apart from the second peak by less than 3 times the spacing between the first peak and the second peak.

The data analyzer 36 can also determine the distance between the first peak and the third peak (a third distance). The third distance may be compared to a third distance criterion to determine if the second timing threshold is satisfied. For example, to satisfy the second timing threshold, the first peak and the third peak may be spaced apart by a minimum distance (in time), such as 0.2 s. That is, the third distance may be not less than the minimum distance (e.g. 0.2 seconds) to satisfy the second timing threshold. In some cases, the minimum distance may be modified based on a user's heart rate.

At 808, the data analyzer 36 may compare the first peak and the second peak to determine if the second peak satisfies the first threshold. For example, in some cases, to satisfy the first threshold, the height of the second peak may be at least 80% of the height of the first peak. In some cases, the height of a peak can refer to the height of that peak above the zero axis.

At 810, the data analyzer 36 may then compare the second peak and the third peak to determine if the third peak satisfies the second threshold. For example, in some cases, to satisfy the second threshold, the height of the third peak may be at least 10% of the height of the second peak.

At 812, the data analyzer 36 may determine if the pulse signal satisfies the error threshold condition. For example, the pulse signal may satisfy the error threshold condition if both the first threshold and the second threshold are satisfied.

Figure 9A:
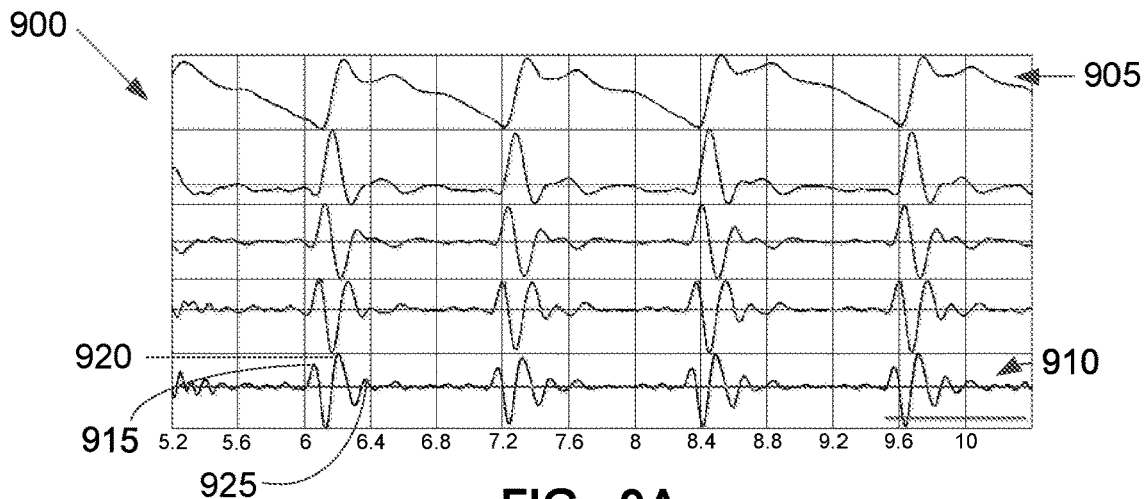
FIG. 9A is a diagram illustrating an example pulse signal and derivatives of the pulse signal where error threshold conditions are satisfied.

Referring now to FIG. 9A, shown therein is a plot 900 of an example pulse signal 905 and a fourth derivative 910 of the pulse signal 905. The x-axis of plot 900 shows time in seconds while the y-axis of plot 900 shows signal amplitude that has been scaled to have values between 0 and 1. In the first pulse of the fourth derivative 910, the first peak 915, second peak 920 and the third peak 925 can be identified. In the examples shown in FIGS. 9A-9C, the error threshold condition requires that the height of the second peak be at least 80% of the height of the first peak to satisfy the first threshold and the height of the third peak be at least 10% of the height of the second peak to satisfy the second threshold.

In plot 900, the second peak 920 is taller than the first peak 915 and thus greater than 80% of the height of the first peak 915. Accordingly, the first threshold is satisfied by this pulse. Furthermore, the third peak 925 is more than 10% of the height of the second peak 920 so the second threshold is also satisfied. As a result, this pulse satisfies the error threshold condition.

Figure 9B:
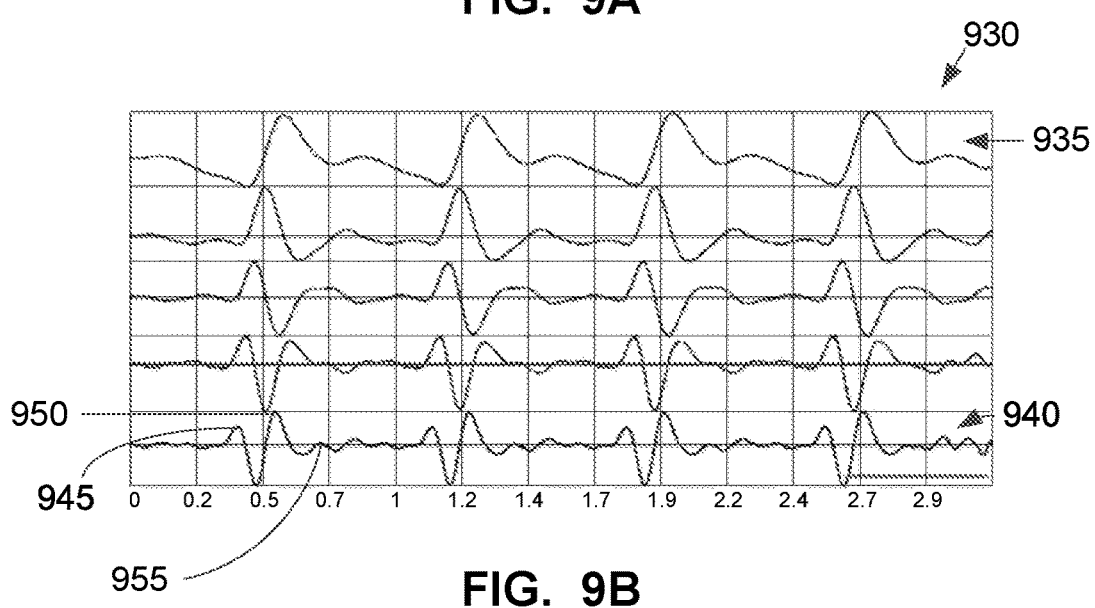
FIG. 9B is a diagram illustrating an example pulse signal and derivatives of the pulse signal where error threshold conditions are not satisfied.

Referring now to FIG. 9B, shown therein is a plot 930 of another example pulse signal 935 and the fourth derivative 940 of the pulse signal 935. The x-axis of plot 930 shows time in seconds while the y-axis of plot 930 shows signal amplitude that has been scaled to have a value of between 0 and 1. In the first pulse of the fourth derivative 940, the first peak 945, second peak 950 and the third peak 955 can be identified.

In plot 930, the height of the third peak 955 is not 10% of the height of the second peak 950. Thus, the second threshold is not satisfied by the pulse signal. Accordingly, the pulse signal 935 shown in plot 930 does not satisfy the error threshold condition. As none of the pulses shown in plot 930 satisfy the error threshold condition, this may suggest that the sensor unit 42 is not placed in a suitable location for recording a pulse signal.

Figure 9C:
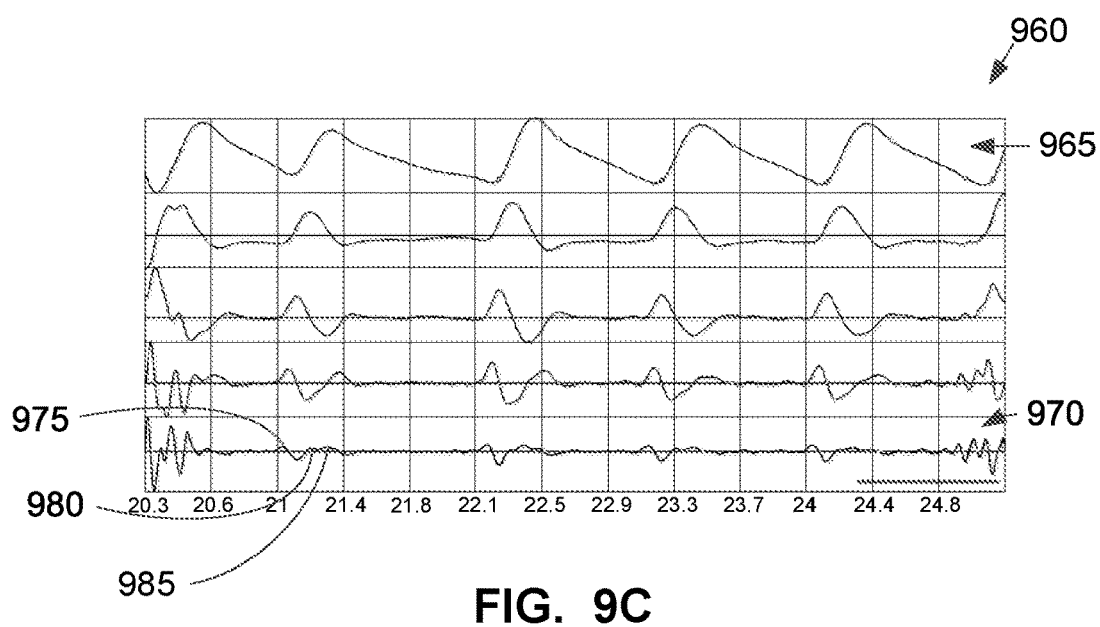
FIG. 9C is a diagram illustrating another example pulse signal and derivatives of the pulse signal where error threshold conditions are not satisfied.

Referring now to FIG. 9C, shown therein is a plot 960 of another example pulse signal 965 and a fourth derivative 970 of the pulse signal 965. The x-axis of plot 960 shows time in seconds while the y-axis of plot 960 shows signal amplitude that has been scaled to have values between 0 and 1. In the first pulse of the fourth derivative 970, the first peak 975, second peak 980 and the third peak 985 can be identified.

In plot 930, the height of the second peak 980 is not 80% of the height of the first peak 975. Thus, the first threshold is not satisfied by the pulse signal. Accordingly, the pulse signal 965 shown in plot 960 does not satisfy the error threshold condition. As none of the pulses shown in plot 960 satisfy the error threshold condition, this may suggest that the sensor unit 42 is not placed in a suitable location for recording a pulse signal.

Figure 10:
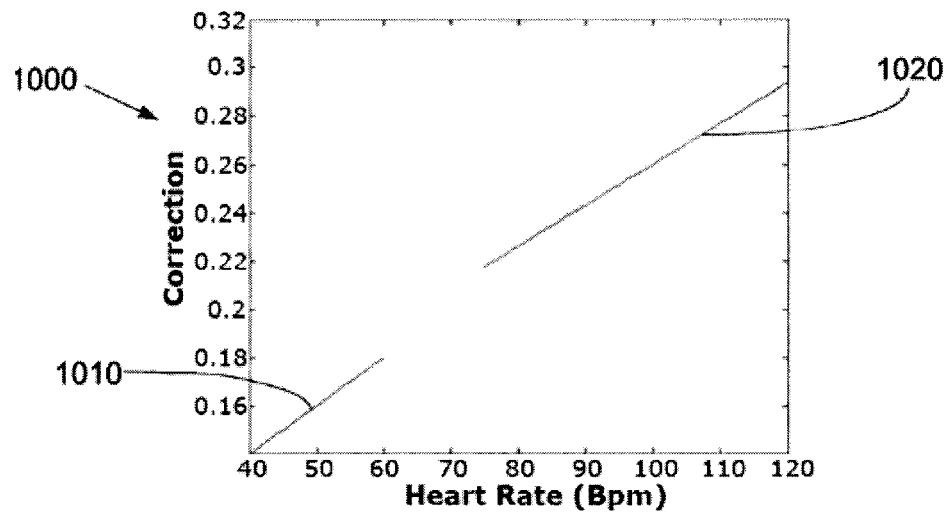
FIG. 10 illustrates a plot of example reflected wave ratio normalization factors that may be used for determining a normalized aortic pulse wave velocity in accordance with an example embodiment.

Referring now to FIG. 10, shown therein is an example plot 1000 of reflected wave ratio normalization factors that may be used to determine a normalized AoPWV. The reflected wave ratio normalization factors may normalize the reflected wave ratio, and thereby the AoPWV based on a user's heart rate. The reflected wave ratio normalization factors may normalize the reflected wave ratio to a baseline heart rate range, for example a heart rate range from 60 Bpm to 75 Bpm.

Figure 11:
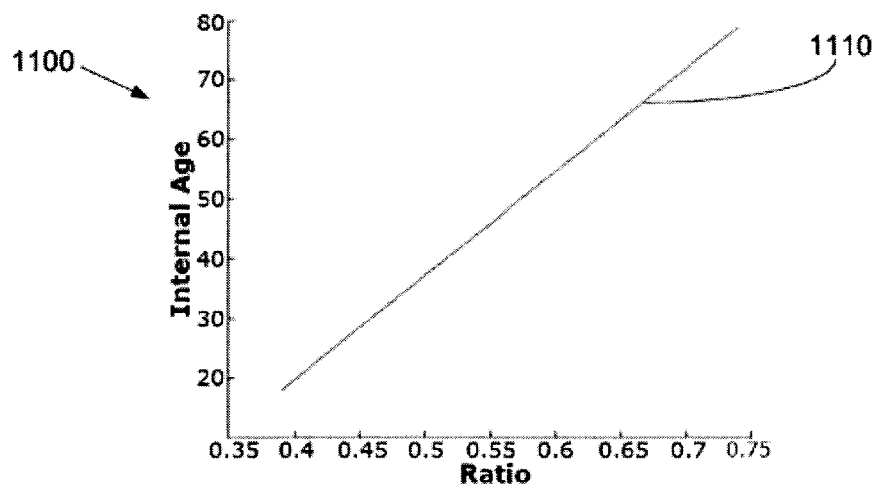
FIG. 11 illustrates a plot of example conversion factors for converting a reflected wave ratio to an internal age measure in accordance with an example embodiment.

The reflected wave ratio normalization factors 1000 shown in FIG. 11 were determined by the inventors by experimental testing on a sample of the population. Pulse signal data was collected over a period of several months from more than 100 different users. A total of over 2000 pulse signal data sets were collected from the users. Each pulse signal data set was used to determine a reflected wave ratio and heart rate. The determined reflected wave ratio was then plotted against the heart rate. As a large number of pulse signal data sets were used, from a varied population, it was assumed that the results provided a cloud of points with a ratio distribution independent from the heart rate.

Outliers were removed, and the cloud of points was analyzed to determine a correlation between the heart rate and the determined reflected wave ratio. In particular, a correlation was determined for higher and lower heart rates—that is heart rates above 75 bpm and below 60 bpm.

The cloud of points was de-trended and used to determine heart rate correction or normalization factors (i.e. making the reflected wave ratio independent from the heart rate). The correction/normalization factors were then validated by testing several subjects representative of individuals of both genders and across age groups.

The validation testing included having test subjects increase their heart rate by performing easy exercises. The individuals were then asked to rest until their heart rate recovered towards a baseline value. A series of pulse signal recordings were determined as the heart rate recovered towards the baseline. For each pulse signal recording, the reflected wave ratio was determined.

The reflected wave ratio results were then analyzed with and without using the normalization factors. As expected, with normalizing the results, the reflected wave ratio varied with heart rate. By contrast, after normalization the reflected wave ratio remained more stable.

As shown in plot 1000, different low heart rate normalization factors 1010 and high or elevated heart rate normalization factors 1020 may be used depending on the user's heart rate. For instance, the normalization factors may be determined to be:

$Ratio_{normalized} = Ratio + 0.09 + 0.0017*(60/beat\ length)$
for elevated heart rates (e.g. heart rate over 75 Bpm), and:

$Ratio_{normalized} = Ratio + 0.06 + 0.002*(60/beat\ length)$
for low heart rates (e.g. heart rates below 60 Bpm).

Referring now to FIG. 11, shown therein is an example plot 1100 of conversion factors 1110 for determining a user's internal age using the reflected wave ratio. As mentioned above, the reflected wave ratio can be used to determine an individual's internal age as well as their AoPWV. Plot 1100 shows an example of the internal age conversion factors 1110 that may be used. It might be noted that the best fit line through the data set shown in FIG. 6 is very slightly exponential while the conversion factors 1110 may be linear. In some cases, for ease of calculation the relationship between reflected wave ratio and internal age can be defined using a linear relationship. In general, the reflected wave ratio used to determine the individual's internal age may be a normalized reflected wave ratio determined as described above. Accordingly, the conversion factors 1110 may be slightly offset from those shown in FIG. 6, as the conversion factors 1110 are generated based on normalized reflected wave ratios.

The conversion factors 1110 shown in plot 1100 correspond to determining an individual's internal age by:

$$Internal\ Age = \frac{(Ratio - 0.2875)}{0.005722}$$

Figure 12:
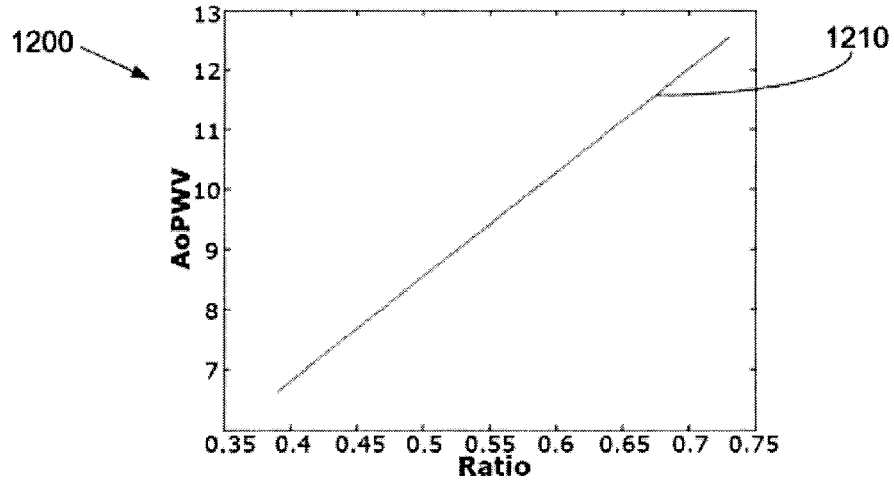
FIG. 12 illustrates a plot of example conversion factors for converting a reflected wave ratio to an aortic pulse wave velocity in accordance with an example embodiment.

Referring now to FIG. 12, shown therein is an example plot 1200 of conversion factors 1210 that may be used in some embodiments to convert a reflected wave ratio (or normalized reflected wave ratio) to AoPWV. The conversion factors 1210 shown in plot 1200 correspond to determining an individual's AoPWV by using the following relation:

$AoPWV = 17.43*Ratio - 0.1714$

Once again, the normalized reflected wave ratio may be used. The AoPWV and/or internal age and/or reflected wave ratio analysis can be repeated for each pulse in the acquired pulse signal. The analysis results may be cleaned (e.g. to remove outliers) and then averaged for the entire pulse signal. This can be used to provide a more accurate and reliable assessment of reflected wave ratio, AoPWV, internal age, BP, etc.

Figure 13:
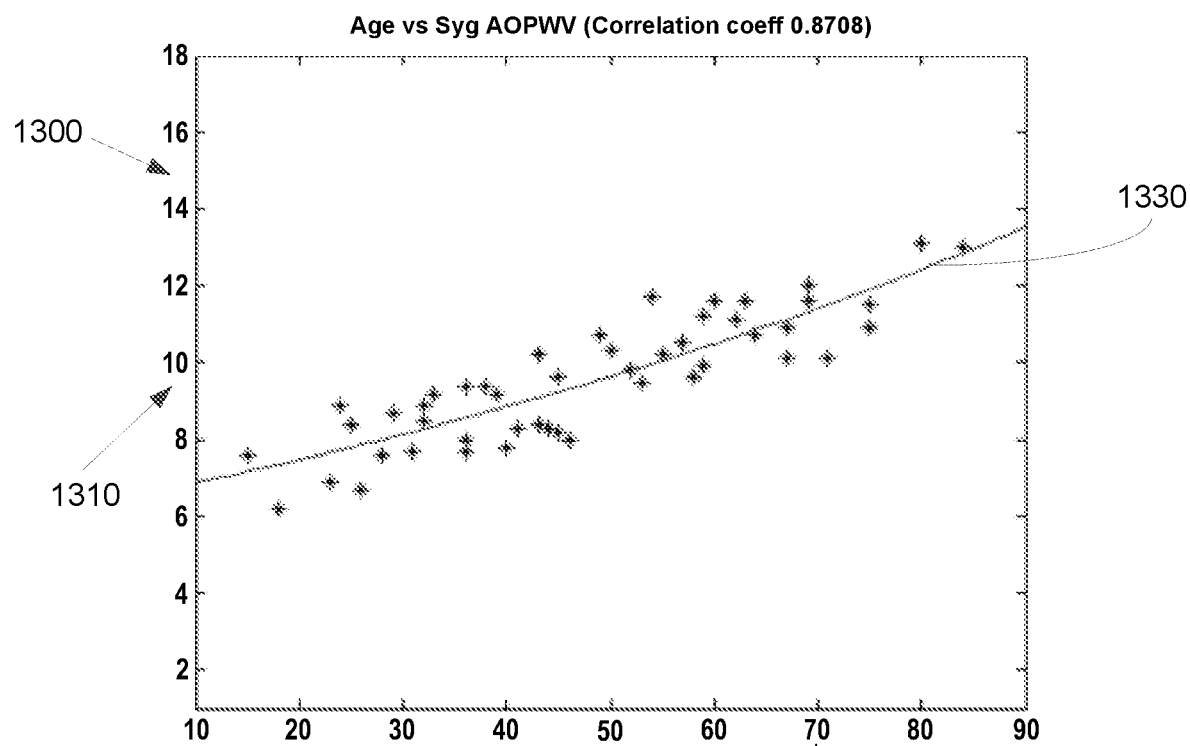
FIG. 13 illustrates a plot of an example of aortic pulse wave velocity determined using an alternative method against age.

Referring now to FIG. 13, shown therein is an example plot 1300 showing the relationship between AoPWV 1310 and an individual's age 1320. As shown in plot 1300, AoPWV 1310 has a generally upward trend 1330 with age 1320 with a correlation coefficient of 0.8708. Plot 1300 was generated by testing individual AoPWV using a SphygmoCor Xcel System from AtCor Medical Pty Limited (for reference, see http://www.atcormedical.com/sphygmocor_xcel.html).

For further examples of the correlation between AoPWV and age see 'Determinants of pulse wave velocity in healthy people and in the presence of cardiovascular risk factors: 'establishing normal and reference values' (available at http://eurheartj.oxfordjournals.org/content/31/19/2338).

Figure 14:
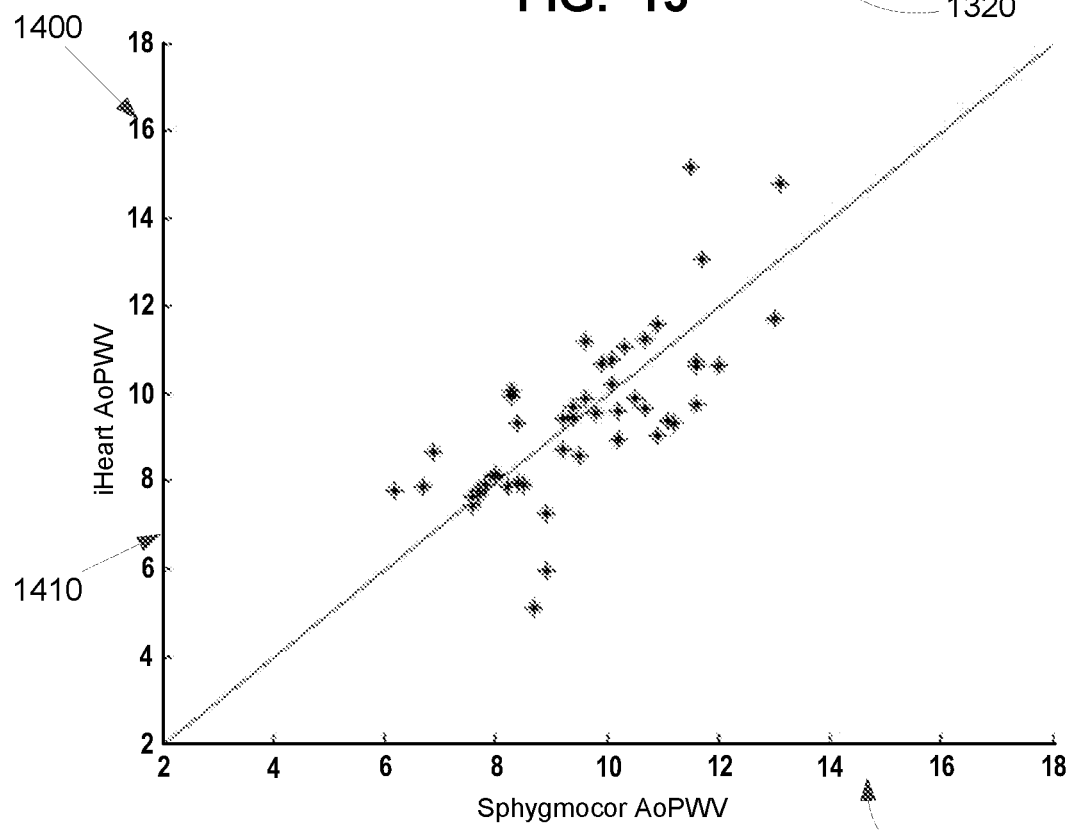
FIG. 14 illustrates a plot of aortic pulse wave velocity (determined in accordance with an example embodiment) compared with aortic pulse wave velocity determined using an alternative method.

Referring now to FIG. 14, shown therein is an example plot 1400 of AoPWV 1410 determined using the methods described herein and AoPWV 1420 obtained using the SphygmoCor Excel System. As plot 1400 illustrates, there appears to be good correlation (a correlation coefficient of 0.7242) between the AoPWV 1410 results determined using the methods described herein and determining AoPWV 1420 using the SphygmoCor Excel System.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

The invention claimed is:

1. A method for monitoring aortic pulse wave velocity, the method comprising:
receiving, by a processor, a pulse signal from a single sensor on the exterior of an individual's body, the single sensor being positioned at a sensor location that allows acquisition of the pulse signal such that an aortic reflected wave component of the pulse signal is present and allows characterization of reflected wave onset;
determining, by the processor, a first derivative from the pulse signal;
determining, by the processor, a third derivative from the pulse signal;
identifying, by the processor, a reflected wave onset point in the pulse signal at a pulse signal location corresponding to a second peak of the third derivative;
determining, by the processor, a reflected wave ratio at the reflected wave onset point by:
identifying, by the processor, a first derivative onset point in the first derivative corresponding in time to the reflected wave onset point in the third derivative; and
determining, by the processor, the reflected wave ratio as a normalized height of the first derivative onset point;
determining, by the processor, the aortic pulse wave velocity from the reflected wave ratio; and
at least one of displaying the aortic pulse wave velocity, transmitting the aortic pulse wave velocity, and storing the aortic pulse wave velocity.

2. The method of claim 1, wherein determining the normalized height of the first derivative onset point comprises:
identifying a first peak in the first derivative;
measuring a height of the first peak;
normalizing the first derivative based on the height of the first peak; and
measuring a height of the normalized first derivative at the first derivative onset point.

3. The method of claim 1, wherein determining the aortic pulse wave velocity comprises:
using a look-up table of mappings from the reflected wave ratio to the aortic pulse wave velocity.

4. The method of claim 1, further comprising:
determining a heart rate from the pulse signal; and
determining a normalized aortic pulse wave velocity using a normalization factor determined from the heart rate.

5. The method of claim 1, wherein the pulse signal is a volume pulse signal.

6. The method of claim 1, further comprising:
calibrating blood pressure factors for the individual; and
determining the individual's blood pressure using the aortic pulse wave velocity and the blood pressure factors.

7. The method of claim 1, further comprising:
prior to identifying the reflected wave onset point, determining if the pulse signal satisfies an error threshold condition; and
only performing the steps of identifying the reflected wave onset point, determining the reflected wave ratio, and determining the aortic pulse wave velocity if the pulse signal satisfies the error threshold condition.

8. The method of claim 7 further comprising:
determining a fourth derivative from the pulse signal;
identifying a first peak, a second peak, and a third peak from the fourth derivative; and
determining if the first peak, second peak, and the third peak from the fourth derivative satisfy a plurality of peak error conditions;
wherein the pulse signal satisfies the error threshold condition if the first peak, second peak, and the third peak from the fourth derivative satisfy the plurality of peak error conditions.

9. The method of claim 8 wherein the plurality of peak error conditions comprise a first threshold and a second threshold, and the method further comprises:
comparing the first peak and the second peak from the fourth derivative to determine if the second peak satisfies the first threshold; and
comparing the second peak and the third peak from the fourth derivative to determine if the third peak satisfies the second threshold;
wherein the pulse signal satisfies the error threshold condition if both the first threshold and the second threshold are satisfied.

10. The method of claim 8, wherein a height of the second peak from the fourth derivative being at least 80% of a height of the first peak satisfies the first threshold; and
a height of the third peak from the fourth derivative being at least 10% of the height of the second peak satisfies the second threshold.

11. The method of claim 8, wherein the plurality of peak error conditions comprise a relative amplitude threshold, a first timing threshold, and a second timing threshold, and the method further comprises:
comparing the first peak and the second peak from the fourth derivative to determine if the second peak satisfies the relative amplitude threshold;
determining a first distance in time between the first peak and the second peak from the fourth derivative and a second distance in time between the second peak and the third peak from the fourth derivative;
comparing the first distance and second distance to determine if the first timing threshold is satisfied; and
determining a third distance between the first peak and the third peak from the fourth derivative to determine if the second timing threshold is satisfied;
wherein the pulse signal satisfies the error threshold condition if each of the relative amplitude threshold, the first timing threshold and the second timing threshold is satisfied.

12. The method of claim 11, wherein:
a height of the second peak from the fourth derivative being at least 80% of a height of the first peak satisfies the relative amplitude threshold;
the second distance being less than three times the first distance satisfies the first timing threshold; and
the third distance not being less than 0.2 seconds satisfies the second timing threshold.

13. A computer readable medium comprising a plurality of instructions that are executable on a microprocessor of a device for adapting the device to implement a method for monitoring aortic pulse wave velocity, wherein the method comprises:
receiving a pulse signal from a single sensor on the exterior of an individual's body, the single sensor being positioned at a sensor location that allows acquisition of the pulse signal such that an aortic reflected wave component of the pulse signal is present and allows characterization of reflected wave onset;
determining a first derivative from the pulse signal;
determining a third derivative from the pulse signal;

identifying a reflected wave onset point in the pulse signal at a pulse signal location corresponding to a second peak of the third derivative;

determining a reflected wave ratio at the reflected wave onset point by:

identifying a first derivative onset point in the first derivative corresponding in time to the reflected wave onset point in the third derivative; and determining the reflected wave ratio as a normalized height of the first derivative onset point;

determining the aortic pulse wave velocity from the reflected wave ratio; and at least one of displaying the aortic pulse wave velocity, transmitting the aortic pulse wave velocity, and storing the aortic pulse wave velocity.

14. The computer readable medium of claim 13, wherein determining the normalized height of the first derivative onset point comprises:

identifying a first peak in the first derivative;

measuring a height of the first peak;

normalizing the first derivative based on the height of the first peak; and measuring a height of the normalized first derivative at the first derivative onset point.

15. The computer readable medium of claim 13, wherein the method further comprises:

calibrating blood pressure factors for the individual; and determining the individual's blood pressure using the aortic pulse wave velocity and the blood pressure factors.

16. A system for monitoring aortic pulse wave velocity, the system comprising:

a pulse acquisition unit configured to acquire a pulse signal from the exterior of an individual's body; and a pulse analysis unit comprising at least one of a display unit, a storage unit and a communication interface;

wherein the pulse acquisition unit includes a single sensor positioned at a sensor location that allows acquisition of the pulse signal such that an aortic reflected wave component of the pulse signal is present and allows characterization of reflected wave onset, and the pulse acquisition unit is further configured to transmit the pulse signal to the pulse analysis unit; and wherein the pulse analysis unit is configured to:

determine a first derivative from the pulse signal;

determine a third derivative from the pulse signal;

identify a reflected wave onset point in the pulse signal at a pulse signal location corresponding to a second peak of the third derivative;

determine a reflected wave ratio at the reflected wave onset point by:

identifying a first derivative onset point in the first derivative corresponding in time to the reflected wave onset point in the third derivative; and determining the reflected wave ratio as a normalized height of the first derivative onset point;

determine the aortic pulse wave velocity from the reflected wave ratio; and at least one of displaying the aortic pulse wave velocity using the display unit, transmitting the aortic pulse wave velocity using the communication interface, and storing the aortic pulse wave velocity in the storage unit.

17. The system of claim 16, wherein the pulse analysis unit is configured to determine the normalized height of the first derivative onset point by:

identifying a first peak in the first derivative;

measuring a height of the first peak;

normalizing the first derivative based on the height of the first peak; and measuring a height of the normalized first derivative at the first derivative onset point.

18. The system of claim 16, wherein the pulse analysis unit is configured to determine the aortic pulse wave velocity by using a look-up table of mappings from the reflected wave ratio to the aortic pulse wave velocity.

19. The system of claim 16, wherein the pulse analysis unit is further configured to:

determine a heart rate from the pulse signal; and determine a normalized aortic pulse wave velocity using a normalization factor determined from the heart rate.

20. The system of claim 16, wherein the pulse acquisition unit is configured to acquire a volume pulse signal.

21. The system of claim 16, wherein the pulse analysis unit is configured to:

calibrate blood pressure factors for the individual; and determine the individual's blood pressure using the aortic pulse wave velocity and the blood pressure factors.

22. The system of claim 16, wherein the pulse analysis unit is further configured to:

determine if the pulse signal satisfies an error threshold condition prior to identifying the reflected wave onset point; and only perform the steps of identifying the reflected wave onset point, determining the reflected wave ratio, and determining the aortic pulse wave velocity if the pulse signal satisfies the error threshold condition.

23. The system of claim 22, wherein the pulse analysis unit is further configured to:

determine a fourth derivative from the pulse signal;

identify a first peak, a second peak, and a third peak from the fourth derivative;

determine if the first peak, second peak, and the third peak from the fourth derivative satisfy a plurality of peak error conditions; and determine that the pulse signal satisfies the error threshold condition if the first peak, second peak, and the third peak from the fourth derivative satisfy the plurality of peak error conditions.

24. The system of claim 23, wherein the plurality of peak error conditions comprise a first threshold and a second threshold, and the pulse analysis unit is configured to:

compare the first peak and the second peak from the fourth derivative to determine if the second peak satisfies the first threshold;

compare the second peak and the third peak from the fourth derivative to determine if the third peak satisfies the second threshold; and determine that the pulse signal satisfies the error threshold condition if both the first threshold and the second threshold are satisfied.

25. The system of claim 23 wherein a height of the second peak from the fourth derivative being at least 80% of a height of the first peak satisfies the first threshold; and a height of the third peak from the fourth derivative being at least 10% of the height of the second peak satisfies the second threshold.

26. The system of claim 23, wherein the plurality of peak error conditions comprise a relative amplitude threshold, a first timing threshold, and a second timing threshold, and the pulse analysis unit is configured to:

compare the first peak and the second peak from the fourth derivative to determine if the second peak satisfies the relative amplitude threshold;

determine a first distance in time between the first peak and the second peak from the fourth derivative and a second distance in time between the second peak and the third peak from the fourth derivative;

compare the first distance and second distance to determine if the first timing threshold is satisfied;

determine a third distance between the first peak and the third peak from the fourth derivative to determine if the second timing threshold is satisfied; and determine that the pulse signal satisfies the error threshold condition if each of the relative amplitude threshold, the first timing threshold and the second timing threshold is satisfied.

27. The system of claim 26, wherein:

a height of the second peak from the fourth derivative being at least 80% of a height of the first peak satisfies the relative amplitude threshold;

the second distance being less than three times the first distance satisfies the first timing threshold; and the third distance not being less than 0.2 seconds satisfies the second timing threshold.

28. The system of claim 22, wherein the pulse analysis unit is further configured to perform at least one of displaying the individual's blood pressure using the display unit, transmitting the individual's blood pressure using the communication interface, and storing the individual's blood pressure in the storage unit.

* * * * *